US006770632B1

(12) United States Patent
Aghi et al.

(10) Patent No.: US 6,770,632 B1
(45) Date of Patent: Aug. 3, 2004

(54) FOLYPOLYGLUTAMYL SYNTHETASE GENE TRANSFER TO ENHANCE ANTIFOLATE

(75) Inventors: Manish Aghi, Brookline, MA (US); Christof M. Kramm, Duesseldorf (DE); Xandra O. Breakefield, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/617,116

(22) Filed: Jul. 14, 2000

Related U.S. Application Data

(60) Provisional application No. 60/144,074, filed on Jul. 16, 1999.

(51) Int. Cl.$^7$ .................. A61K 31/70; A61K 48/00; C12N 15/63; C12N 15/87; C12N 15/86
(52) U.S. Cl. ............... 514/44; 424/93.2; 435/320.1; 435/455; 435/456; 435/458; 435/459
(58) Field of Search .................. 514/44; 435/320.1, 435/455, 456, 458, 375; 424/93, 2

(56) References Cited

U.S. PATENT DOCUMENTS

| | | | |
|---|---|---|---|
| 5,529,774 A | 6/1996 | Barba et al. | 424/93.21 |
| 5,591,624 A | 1/1997 | Barber et al. | 435/240.2 |
| 5,601,818 A | 2/1997 | Freeman et al. | 424/93.21 |
| 5,631,236 A | 5/1997 | Woo et al. | 514/44 |
| 5,670,488 A | 9/1997 | Gregory et al. | 514/44 |
| 5,688,773 A | 11/1997 | Chiocca et al. | 514/44 |
| 5,691,177 A | 11/1997 | Guber et al. | 435/172.3 |
| 5,741,486 A | 4/1998 | Pathak et al. | 424/93.21 |
| 5,763,216 A | * 6/1998 | Moscow et al. | 435/69.1 |
| 5,763,217 A | 6/1998 | Cynader et al. | 435/69.1 |
| 5,763,242 A | 6/1998 | Zhang et al. | 435/172.3 |

FOREIGN PATENT DOCUMENTS

WO    WO 95/06486    3/1995

OTHER PUBLICATIONS

Miller et. al.; Targeted vectors for gene therapy, 1995, FASEB. J. 9: 190–199.*

Verma et. al.; Gene therapy–promises, problems and prospects, 1997, Nature vol. 389: 238–242.*

Dang et. al.; Gene Therapy and Translational Cancer Research, 1999, Clinical Cancer Research vol. 5: 471–474.*

Deonarain; Ligand–targeted receptor–mediated vectors for gene delivery, 1998, Exp. Opin. Ther. Patents 8(1): 53–69.*

Osborne; Regulation of Folate and One–carbon Metabolism in Mammalian Cells, 1993, The Journal of Biological Chemistry, vol. 268, No. 29: 21657–21664.*

Spinella et al., Molecular cloning of murine folypoly–gamma–glutamate synthetase, 1996, Biochemical Biophysical Acta, 1305(1–2): 11–4.*

Hollon, T. Researchers and regulators reflect on first gene therapy death. Nature Medicine 6, p. 6, 2000.*

Pawelek et al. Tumor–targeted Salmonella as a novel anti-cancer vector. Cancer Res. 57:4537–4544, 1997.*

Filion et al. Major limitations in the use of cationic liposomes for DNA delivery. International Journal of Pharmaceutics 162: 159–170, 1998.*

Scherman et al. Application of lipids and plasmid design for gene delivery to mammalian cells. Curr. Opin. Biotechnol. 9:480–485, 1998.*

Romano et al. Latest development in gene transfer technology: Achievements, perspectives, and controversies over therapeutic applications. Stem Cells 18: 19–39, 2000.*

Greco et al. Gene directed enzyme/prodrug therapy of cancer: Historical appraisal and future prospectives. Journal of Cellular Physiology 187:22–36, 2001.*

Xu et al. Strategies for enzyme/prodrug cancer therapy. Clin. Cancer Res. 7:3314–3324, 2001.*

Abdallah, B. et al., "Non–viral gene transfer: Applications in developmental biology and gene therapy," *Biol. Cell* 85:1–7 (1995).

Aghi, M. et al., "Synergistic Anticancer Effects of Ganciclovir/Thymidine Kinase and 5–Fluorocytosine/Cytosine Deaminase Gene Therapies," *J. Natl. Cancer Inst.* 90:370–380 (Mar. 1998).

Aghi, M. et al., "Folylpolyglutamyl Synthetase Gene Transfer and Glioma Antifolate Sensitivity in Culture and In Vivo," *J. Natl. Cancer Inst.* 91:1233–1241 (Jul. 1999).

Aghi, M. et al., "Prodrug activation enzymes in cancer gene therapy," *J. Gene Med.* 2:148–164 (May–Jun. 2000).

Barredo, J. and Moran, R.G., "Determinants of Antifolate Cytotoxicity: Folylpolyglutamate Synthetase Activity during Cellular Proliferation and Development," *Molec. Pharmacol.* 42:687–694 (1992).

Calos, M.P. et al., "The potential of extrachromosomal replicating vectors for gene therapy," *Trends in Genetics* 12:463–467 (1996).

Chabner, B.A. et al., "Polyglutamation of Methotrexate," *J. Clin. Invest.* 76:907–912 (1985).

Chase, M. et al., "An oncolytic viral mutant that delivers the CYP2B1 transgene and augments cyclophosphamide chemotherapy," *Nature Biotechnol.* 16:444–448 (1998).

Chen, L. and Waxman, D.J., "Intratumoral Activation and Enhanced Chemotherapeutic Effect of Oxazaphosphorines following Cytochrome P–450 Gene Transfer: Development of a Combined Chemotherapy/Cancer Gene Therapy Strategy," *Cancer Res.* 55:581–589 (1995).

(List continued on next page.)

*Primary Examiner*—David Guzo
*Assistant Examiner*—Quang Nguyen
(74) *Attorney, Agent, or Firm*—Sterne, Kessler, Goldstein & Fox PLLC

(57) ABSTRACT

Methods of killing neoplastic cells are provided. The invention relates to the use of folylpolyglutamyl synthetase (FPGS) gene transfer to enhance the sensitivity of several types of tumor cells to polyglutamylatable antifolate drugs, such as methotrexate (MTX) and edatrexate (EDX).

21 Claims, 6 Drawing Sheets

OTHER PUBLICATIONS

Chu, E. and Allegra, C.J., "Antifolates," *Cancer Chemotherapy and Biotherapy: Principles and Practice*, 2$^{nd}$ Edition, Chabner, B.A. and Longo, D.L., eds., Lippincott–Raven Publishers, New York, NY, pp. 109–148 (1996).

Dachs, G.U. et al., "Targeting Gene Therapy to Cancer: A Review," *Oncol. Res.* 9:313–325 (1997).

Danks, M.K. et al., "Overexpression of a Rabbit Liver Carboxylesterase Sensitizes Human Tumor Cells to CPT–11," *Cancer Res.* 58:20–22 (Jan. 1998).

Deonarain, M.P. et al., "Genetic Delivery of Enzymes for Cancer Therapy," *Gene Therapy* 2: 235–244 (1995).

Drinkard, L. et al., "A Phase II Trial of Edatrexate (ETX) in Progressive Malignant Glioma (PMG)," *Program/Proceedings of the American Soc. of Clinical Oncology* 13:182, Abstract No. 517 (1994).

Freeman, S.M. et al., "The 'Bystander Effect': Tumor Regression When a Fraction of the Tumor Mass Is Genetically Modified," *Cancer Res.* 53:5274–5283 (1993).

Freeman, S.M. et al., "In Situ Use of Suicide Genes for Cancer Therapy," *Semin. Oncology* 23:31–45 (1996).

Freemantle, S.J. and Moran, R.G., "Transcription of the Human Folylpoly–y–glutamate Synthetase Gene," *J. Biol. Chem.* 272:25373–25379 (1997).

Fry, D.W. et al., "Analysis of the Role of Membrane Transport and Polyglutamation of Methotrexate in Gut and the Ehrlich Tumor in Vivo as Factors in Drug Sensitivity and Selectivity," *Cancer Res.* 43: 1087–1092 (1983).

Garrow, T.A. et al., "Expression cloning of a human cDNA encoding folylpoly(λ–glutamate) synthetase and determination of its primary structure," *Proc. Natl. Acad. Sci. USA* 89:9151–9155 (1992).

Kim, J. S. et al., "Regulation of Folate and One–carbon Metabolism in Mammalian Cells," *J. Biol. Chem.* 268:21680–21685 (1993).

Lan, K–H, et al., "In Vivo Selective Gene Expression and Therapy Mediated by Adenoviral Vectors for Human Carcinoembryonic Antigen–producing Gastric Carcinoma," *Cancer Res.* 57:4279–4284 (1997).

Li, W.–W. et al., "Mechanisms of Natural Resistance to Antifolates in Human Soft Tissue Sarcomas," *Cancer Res.* 52:1434–1438 (1992).

Matherly, L.H. et al., "Antifolate Polyglutamylation and Competitive Drug Displacement at Dihydrofolate Reductase as Important Elements in Leucovorin Rescue in L1210 Cells," *Cancer Res.* 46:588–593 (1986).

McGuire, J.J. and Russell, C.A., "Folylpolyglutamate Synthetase Expression in Antifolate–Sensitive and –Resistant Human Cell Lines," *Oncology Res.* 10:193–200 (1998).

Miller, N. and Whelan, J., "Progress in Transcriptionally Targeted and Regulatable Vectors for Genetic Therapy," *Hum. Gene Ther.* 8:803–815 (1997).

Moolten, F.L., "Drug sensitivity ("suicide") genes for selective cancer chemotherapy," *Cancer Gene Ther.* 1:279–287 (1994).

Murdoch, B. et al., "A rapid screening procedure for the identification of high–titer retrovirus packaging clones," *Gene Ther.* 4:744–749 (1997).

Nakanishi, M. et al., "Gene Introduction Into Animal Tissues," *Crit. Rev. Therapeut. Drug Carrier Systems* 12:263–310 (1995).

O'Malley, Jr., B.W. et al., "Combination Gene Therapy for Oral Cancer in a Murine Model," *Cancer Res.* 56:1737–1741 (1996).

O'Malley, Jr., B.W. and Li, D., "Combination Gene Therapy for Salivary Gland Cancer," *Ann. N.Y. Acad. Sci.* 842:163–170 (Apr. 1998).

Peters, G.J. and van der Wilt, C.L., "Development of a Simple Folylpolyglutamate Synthetase Assay in Tissues and Cell Lines," in *Chemistry and biology of Pteridines and Folates*, Ayling, J.E. et al., eds., Plenum Press, NY, pp. 651–654 (1993).

Pizzorno, G. et al., "Impaired Polyglutamylation of Methotrexate as a Cause of Resistance in CCRF–CEM Cells after Short–Term, High Dose Treatment with This Drug," *Cancer Res.* 48:2149–2155 (1988).

Rainov, N.G. et al., "Retrovirus–Mediated Gene Therapy of Experimental Brain Neoplasms Using the Herpes Simplex Virus—Thymidine Kinase/Ganciclovir Paradigm," *Cancer Gene Therapy* 3:99–106 (1996).

Ram, Z. et al., "In Situ Retroviral–mediated Gene Transfer for the Treatment of Brain Tumors in Rats," *Cancer Res.* 53:83–88 (1993).

Rancourt, C. et al., "Endothelial Cell Vehicles for Delivery of Cytotoxic Genes as a Gene Therapy Approach for Carcinoma of the Ovary," *Clin. Cancer Res.* 4:265–270 (Feb. 1998).

Robbins, P.D. et al., "Viral vectors for gene therapy," *TIBTECH* 16:35–40 (Jan. 1998).

Rogulski, K.R. et al., "Glioma Cells Transduced with an *Escherichia coli* CD/HSV–1 TK Fusion Gene Exhibit Enhanced Metabolic Suicide and Radiosensitivity," *Human Gene Ther.* 8:73–85 (1997).

Roth, J.A. et al., "Retrovirus–Mediated Wild–Type p53 Gene Transfer to Tumors of Patients with Lung Cancer," *Nature Med.* 2:985–991 (1996).

Roth, J.A. and Cristiano, R.J., "Gene Therapy for Cancer: What Have We Done and Where are we Going?" *J. Natl. Cancer Inst.* 89:21–39 (1997).

Roy, K. et al., "Different Antifolate–resistant L1210 Cell Variants with either Increased or Decreased Folylpolyglutamate Synthetase Gene Expression at the Level of mRNA Transcription," *J. Biol. Chem.* 270:26918–26922 (1995).

Roy, K. et al., "Posttranscriptionally Mediated Decreases in Folylpolyglutamate Synthetase Gene Expression in Some Folate Analogue–resistant Variants of the L1210 Cell," *J. Biol. Chem.* 272:6903–6908 (1997).

Rumberger, B.G. et al., "Differing Specificities for 4–Aminofolate Analogues of Folypolyglutamyl Synthetase from Tumors and Proliferative Intestinal Epiethelium of the Mouse with Significance for Selective Antitumor Action," *Cancer Res.* 50:4639–4643 (1990).

Samuels, L.L. et al., "Similar Differential for Total Polyglutamylation and Cytotoxicity among Various Folate Analogues in Human and Murine Tumor Cells in Vitro," *Cancer Res.* 45: 1488–1495 (1985).

Takemura, Y. and Jackman, A.L., "Folate–based thymidylate synthase inhibitors in cancer chemotherapy," *Anti–Cancer drugs* 8:3–16 (1997).

Takemura, Y. et al., "Altered Expression of Folylpolyglutamate Synthetase (FPGS) Gene in Human Leukaemia Cells with Defective Polyglutamation of Raltitrexed (ZD1694)," *Brit. J. Cancer 75(suppl. 1)*:31, Abstract No. P52 (1997).

Taylor, S.M. et al., "Structural Organization of the Human Folylpoly-µ-glutamate Synthetase Gene: Evidence for a Single Genomic Locus," *Cancer Res. 55*: 6030–6034 (1995).

Terzis, A.J.A. et al., "Proliferation, Migration and Invasion of Human Glioma Cells Exposed to Antifolate Drugs," *Int. J. Cancer 54*:112–118 (1993).

Uckert, W. et al., "Double Suicide Gene (Cytosine Deaminase and Herpes Simplex Virus Thymidine Kinase) but Not Single Gene Transfer Allows Reliable Elimination of Tumor Cells in Vivo," *Human Gene Ther. 9*:855–865 (Apr. 1998).

Wei, M.X. et al., "Experimental Tumor Therapy in mice Using the Cyclophosphamide–Activating Cytochrome P450 2B1 Gene," *Hum. Gene Ther. 5*:969–978 (1994).

Yu, J.S. et al., "Retroviral Delivery and Tetracycline–dependent Expression of IL–1β–converting Enzyme (ICE) in a Rat Glioma Model Provides Controlled Induction of Apoptotic Death in Tumor Cells," *Cancer Res. 56*:5423–5427 (1996).

Zhang, J. and Russell, S.J., "Vectors for cancer gene therapy," *Cancer & Metastasis Rev. 15*: 385–401 (1996).

Zufferey, R. et al., "Multiply attenuated lentiviral vector achieves efficient gene delivery in vivo," *Nature Biotechnol. 15*:871–875 (1997).

\* cited by examiner

▲ 9L
◇ 1% 9L/FPGS
□ 10% 9L/FPGS
△ 20% 9L/FPGS
● 9L/FPGS

1

FOLYPOLYGLUTAMYL SYNTHETASE GENE TRANSFER TO ENHANCE ANTIFOLATE

CROSS-REFERENCE TO RELATED APPLICATIONS

This application claims the benefit of U.S. Provisional Application No. 60/144,074, filed on Jul. 16, 1999, which is herein incorporated by reference.

STATEMENT AS TO RIGHTS TO INVENTIONS MADE UNDER FEDERALLY-SPONSORED RESEARCH AND DEVELOPMENT

The U.S. Government has a paid-up license in this invention and the right in limited circumstances to require the patent owner to license others on reasonable terms as provided for by the terms of grant number PO1CA69246, awarded by the National Institutes of Health.

BACKGROUND OF THE INVENTION

1. Field of the Invention

The present invention is directed to the killing of neoplastic cells. More specifically, the present invention relates to the use of folylpolyglutamyl synthetase (FPGS) gene transfer to enhance antifolate drug sensitivity.

2. Related Art

Because of the critical role of folate coenzymes in the synthesis of DNA precursors, folate antagonists (antifolates) have found widespread use as chemotherapeutic agents. Methotrexate (MTX), a 4-aminofolate analogue, has been in clinical use for the treatment of various human malignancies, especially leukemias and breast cancer, for about 40 years. For a review, see Chu, E. and Allegra, C, "Antifolates," in *Cancer Chemotherapy and Biotherapy: Principles and Practice*, Chabner et al, eds., Lippincott-Raven, Philadelphia (1996), pp. 109–148.

MTX is a potent inhibitor of dihydrofolate reductase (DHFR). Inhibition of this enzyme prevents the reduction of dihydrofolate that accumulates in cells actively synthesizing thymaidylate via the thymidylate synthetase reaction. The cells subsequently become depleted of reduced folate cofactors, needed for synthesis of thymidylate and for de novo purine synthesis. The ensuing disruption of DNA replication leads to cell death in actively replicating cells found in tumors and some normal tissues.

Naturally occurring folates and some antifolates, including MTX, possess a single terminal benzoylglutamate residue and are converted intracellularly from monoglutamates into polyglutamates through the action of an enzyme, folylpolyglutamyl synthetase (FPGS), that attaches up to six glutamyl groups in γ-peptide linkage to the terminal benzoylgutamate. Polyglutamylation of folates and antifolates causes two effects. First, polyglutamylation causes intracellular accumulation of folates and antifolates because the highly ionized polyglutamylated forms are not readily transported across cell membranes. For example, MTX polyglutamates efflux out of cells 70 times slower than the monoglutamylated drug (Balinska, M., et al., *Cancer Research* 41:2751–2756 (1981)). Second, polyglutamylation enhances the affinity of folates for the enzymes that utilize them as cofactors, and increases the affinity (and inhibitory effect) of antifolates for their target enzymes, as well as expanding the range of enzymes which antifolates inhibit.

Because MTX is polyglutamylated much more inefficiently than naturally occurring folates, reductions in FPGS activity that have little effect on folate polyglutamate pools can have marked effects on the level of MTX polyglutamates and thus, on the cytotoxicity of MTX. The ability to generate MTX polyglutamates correlates directly with sensitivity to MTX for both human and murine tumor cells (Samuels, L. L., et al., *Cancer Research* 45:1488 (1985)). Human leukemia cell lines that have become resistant to clinically relevant antifolate doses through mutations in FPGS have been described (Pizzorno, G., et al., *Cancer Research* 48:2149 (1988); Roy, K., et al., *Journal of Biological Chemistry* 270:26918–26922 (1995); Roy, K., et al., *Journal of Biological Chemistry* 272:6903–6908 (1997); Takemura, Y., et al., *British Journal of Cancer* 75 (suppl. 1):31 (1997)). Human soft tissue sarcomas have been found to be intrinsically resistant to MTX as a result of low FPGS activity (Li, W. W., et al., *Cancer Research* 52:1434–1438 (1992)). Leukemias that have developed MTX resistance have been removed from patients and found to have impaired drug polyglutamylation (Rodenhuis, S., et al., *Cancer Research* 46:6513–6519(1986)). In addition, antifolates exhibiting the most therapeutic selectivity in murine tumor models consistently display a greater differential in accumulation of the polyglutamylated drug in tumor compared to normal proliferative tissues (Rumberger, S. et al., *Cancer Research* 50:4639–4643 (1990)).

Transfection of mutant CHO cells lacking FPGS activity with an FPGS expression cassette has been shown to increase the sensitivity of these cells to 4 hour MTX pulses in cell culture (Kim, J. S., et al., *Journal of Biological Chemistry* 268:21680–21685 (1993)). However, the question of whether tumor cells which already possess intermediate FPGS activity will show a similar enhancement of MTX sensitivity after FPGS gene delivery has not been previously addressed.

Traditional methods for cancer treatment rely on a combination of surgery, radiation, and cytotoxic chemotherapeutic drugs. Although the treatment of tumor cells with chemotherapeutic drugs is well-known in the art, presently, the therapeutic activity of many cytotoxic anti-cancer drugs is limited by a moderate therapeutic index associated with nonspecific toxicity toward normal host tissues, such as bone marrow, and the emergence of drug-resistant tumor cell sub-populations. One recent approach to enhancing the selectivity of cancer chemotherapeutics, and thereby reducing the toxicity of treatment, involves the application of gene therapy technologies to cancer treatment. See, Roth, J. A. and Cristiano, R. J., *J. Natl. Cancer Inst.* 89:21–39 (1997); Rosenfeld, M. E. and Curiel, D. T., *Curr. Opin. Oncol.* 8:72–77 (1996).

In one such therapy known in the art, the phenotype of the target tumor cells is genetically altered to increase the tumor's drug sensitivity and responsiveness. One strategy being actively investigated involves directly transferring a "chemosensitization" or "suicide" gene encoding a prodrug activation enzyme to malignant cells, in order to confer sensitivity to otherwise innocuous agents (Moolten, F. L., *Cancer Gene Therapy* 1:279–287 (1994); Freeman, S. M., et al., *Semin. Oncol.* 23:3145 (1996); Deonarain, M. P., et al., *Gene Therapy* 2: 235–244 (1995)).

Several prodrug activation genes have been studied for application in cancer gene therapy. The two most extensively investigated prodrug-activating enzymes are herpes simplex virus thymidine kinase (HSV-TK), which activates the prodrug ganciclovir, and *E. coli* cytosine deazninase (CD), which activates the prodrug 5-fluorocytosine (Roth, J. A., Cristiano, R. J., *Journal of the National Cancer Institute* 89:21–39 (1997); Aghi, M., et al., *Journal of the National Cancer Institute* 90:370–380 (1998)).

HSV-TK phosphorylates the prodrug ganciclovir and generates nucleoside analogs that induce DNA chain termination and cell death in actively dividing cells. Tumor cells transduced with HSV-TK acquire sensitivity to ganciclovir, a clinically proven agent originally designed for treatment of viral infections. Moolten, F. L. and Wells, J. M., *J. Natl. Cancer Inst.* 82:297–300 (1990); Ezzeddine, Z. D., et al., *New Biol.* 3:608–614 (1991).

The bacterial gene cytosine deaminase (CD) is a prodrug/enzyme activation system that has been shown to sensitize tumor cells to the antifungal agent 5-fluorocytosine as a result of its transformation to 5-flurouracil, a known cancer chemotherapeutic agent (Mullen, C. A., et al., *Proc. Natl. Acad. Sci. USA* 89: 33–37 (1992); Huber, B. E., et al., *Cancer Res.* 53:4619–4626 (1993); Mullen, C. A., et al., *Cancer Res.* 54:1503–1506 (1994)). Recent studies using these drug susceptibility genes have yielded promising results. See, e.g., Caruso, M., et al., *Proc. Natl. Acad. Sci. USA* 90:7024–7028 (1993); Oldfield, E., et al., *Hum. Gene Ther.* 4: 39 (1993); Culver, K, *Clin. Chem* 40: 510 (1994); O'Malley, Jr., B. W., et al., *Cancer Res.* 56:1737–1741 (1996); Rainov, N. G., et al., *Cancer Gene Therapy* 3:99–106 (1996).

Several other prodrug-activating enzyme systems have also been investigated (T. A. Connors, *Gene Ther.* 2:702–709 (1995)). These include the bacterial enzyme carboxypeptidase G2, which does not have a mammalian homolog, and can be used to activate certain synthetic mustard prodrugs by cleavage of a glutamic acid moiety to release an active, cytotoxic mustard metabolite (Marais, R., et al., *Cancer Res.* 56: 47354742 (1996)), and *E. coli* nitro reductase, which activates the prodrug CB 1954 and related mustard prodrug analogs (Drabek, D., et al., *Gene Ther.* 4:93–100 (1997); Green, N. K., et al., *Cancer Gene Ther.* 4:229–238 (1997)), some of which may be superior to CB1954 (Friedlos, F. et al., *J Med Chem* 40:1270–1275 (1997)). The principle underlying these approaches to prodrug activation gene therapy is that transduction of a tumor cell population with the foreign gene confers upon it a unique prodrug activation capacity, and hence a chemosensitivity which is absent from host cells that do not express the gene.

Current gene therapy technologies are limited by their inability to deliver prodrug activation or other therapeutic genes to a population of tumor cells with 100% efficiency. The effectiveness of this cancer gene therapy strategy can be greatly enhanced, however, by using drugs that exhibit a strong "bystander effect" (Pope, I. M., et al., *Eur J Cancer* 33:1005–1016 (1997)). Bystander cytotoxicity results when active drug metabolites diffluse or are otherwise transferred from their site of generation within a transduced tumor cell to a neighboring, naive tumor cell. Ideally, the bystander effect leads to significant tumor regression even when a minority of tumor cells is transduced with the prodrug activation gene (e.g., Chen, L., et al., *Hum Gene Ther.* 6:1467–1476(1995); Freeman, S., et al., *Cancer Res.* 53:5274–5283 (1993)). Bystander cytotoxic responses may also be mediated through the immune system, following its stimulation by interleukins and other cytokines secreted by tumor cells undergoing apoptosis (Gagandeep, S., et al., *Cancer Gene Ther.* 3:83–88 (1996)).

Although the ganciclovir/HSV-TK and 5-fluorocytosine/CD systems have shown promise in preclinical studies, and clinical trials are underway (Eck, S. L., et al., *Hum Gene Ther.* 7:1465–1482 (1996); Link, C. J. et al., *Hum Gene Ther.* 7:1161–1179 (1996); Roth, J. A., and Cristiano, R. J., *J Natl Cancer Inst.* 89:21–39 (1997)), several limitations restrict their efficacy and limit their application to cancer chemotherapeutics. These include: (a) the non-mammalian nature of the HSV/TK and CD genes, whose gene products may elicit immune responses that interfere with prodrug activation; (b) their reliance on drugs which were initially developed as antiviral drugs (ganciclovir) or antifungal drugs (5-fluorocytosine) and whose cancer chemotherapeutic activity is uncertain; (c) the dependence of these gene therapy strategies on ongoing tumor cell DNA replication; and (d) the requirement, in the case of HSV-TK, for direct cell-cell contact to elicit an effective bystander cytotoxic response (Mesnil, M., et al., *Proc. Natl. Acad Sci. USA.* 93: 1831–1835 (1996)). These considerations, together with the general requirement of combination chemotherapies to achieve effective, durable clinical responses, necessitates the development of alterative strategies to treat cancers using suicide gene-based (prodrug activation) gene therapy.

More recently, a drug activation/gene therapy strategy has been developed based on a cytochrome P450 gene ("CYP" or "P450") in combination with a cancer chemotherapeutic agent that is activated through a P450-catalyzed monoxygenase reaction (Chen, L. and Waxman, D. J., *Cancer Research* 55:581–589 (1995); Wei, M. X., et al., *Hum. Gene Ther.* 5:969–978 (1994); U.S. Pat. No. 5,688,773, issued Nov. 18, 1997). Unlike the prodrug activation strategies mentioned above, the P450-based drug activation strategy utilizes a mammalian drug activation gene (rather than a bacterially or virally derived gene), and also utilizes established chemotherapeutic drugs (i.e., cyclophosphamnide) widely used in cancer therapy.

While MTX's well-established chemotherapeutic activity also distinguishes it from prodrugs such as ganciclovir and 5-fluorocytosine, MTX possesses troublesome toxicity to normal tissues and its effectiveness could be improved by a gene transfer strategy that enhances the drug's selective toxicity.

Thus, in light of the foregoing, there is a need in the art for a method that will enhance a neoplastic cell's sensitivity to MTX or any other polyglutamylatable antifolate drug, and reduce the toxicity to normal tissues and cells.

SUMMARY OF THE INVENTION

The inventors have discovered that by introducing a FPGS gene (and thus an FPGS gene product) into neoplastic cells, the enzymatic conversion of an antifolate drug to its therapeutically active metabolites is greatly enhanced within the cellular and anatomic locale of the tumor, thereby increasing both the selectivity and efficiency with which neoplastic cells are killed. At the same time, undesirable side-effects to normal host cells are minimized.

The inventors first determined if transfection of an experimental brain tumor cell line with an expression cassette bearing the FPGS cDNA would increase the cells' sensitivity to brief MTX pulses in culture. The ability of MTX to cause bystander killing of nontransfected tumor cells in cocultures of nontransfected and transfected cells was then ascertained. The next step involved determining if tumors formed by the transfected cells were more sensitive to reduced frequency of treatment in vivo than tumors formed by the nontransfected tumor cells. Finally, antifolates other than MTX were evaluated by treating the two cell lines and cocultures with brief pulses and by treating homogeneous and mixed tumors in vivo in order to determine what properties are desirable in drugs used in conjunction with FPGS gene delivery.

Accordingly, the present invention overcomes the disadvantages of the prior art by providing a method for killing neoplastic cells, the method comprising: (a) infecting the neoplastic cells with a vector for gene delivery, the vector comprising a folylpolyglutamyl synthetase (FPGS) gene; (b) treating the neoplastic cells with a chemotherapeutic agent that is activated by the product of the FPGS gene; and (c) killing the neoplastic cells.

The invention also provides a preferred embodiment of the foregoing methods wherein the FPGS gene is a mammalian gene, although the FPGS gene from any species could be used. The human FPGS gene is particularly preferred.

In another preferred embodiment of the foregoing methods, the FPGS-activated chemotherapeutic agent is a polyglutamylatable antifolate drug. Examples of such antifolate drugs include methotrexate (MTX), edatrexate (EDX), aminopterin, as well as antifolates which inhibit thymidylate synthetase. MTX and EDX are particularly preferred.

In another preferred embodiment of the foregoing methods, the neoplastic cells are malignant cells that are sensitive to antifolate chemotherapy, such as breast cancer and colon cancer. However, any neoplastic cell can be targeted since FPGS gene delivery will enhance the drug's anticancer effect. Thus, neoplastic cells, such as, e.g., central nervous system tumors (gliomas, astocytomas), lymphomas, lung cancer, melanoma, pancreatic cancer, ovarian cancer, prostate cancer, liver cancer, which are not typically treated with antifolate drugs, will be able to be used in the method of the invention.

The invention also provides a very particularly preferred embodiment of the foregoing methods, wherein the FPGS gene is the human FPGS gene and the chemotherapeutic agent is MTX.

The invention also provides a preferred embodiment of the foregoing methods, wherein the FPGS gene is delivered using a viral vector, preferably viral vectors whose use for gene therapy is well-established for those skilled in the art. Examples of such viral vectors include retrovirus (including lentivirus), adenovirus, adeno-associated virus, herpes virus (including herpes simplex virus I and II and Epstein Barr virus), poliovirus, papillomavirus, or hybrid vectors having attributes of two or more viruses. Retroviruses, adenoviruses, and herpes viruses are particularly preferred viral vectors.

In another embodiment of the foregoing methods, the FPGS gene is delivered using any non-viral vector, preferably one whose use for gene therapy is well-established for those skilled in the art. Examples of such non-viral vectors for gene delivery include prokaryotic vectors (including tumor targeted bacterial vectors), cationic liposomes, DNA-protein complexes, non-viral T7 autogene vectors, fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburst polyamidoamine dendrimers, cationic peptides, and mammalian artificial chromosomes.

In addition, the present invention provides an embodiment of the foregoing methods wherein the FPGS gene is delivered using any cellular vector, preferably one whose use for gene therapy is well-established for those skilled in the art. Examples of such cellular vectors for gene therapy include endothelial cells and macrophages including tumor-infiltrating macrophages, each of which may be modified using viral or non-viral vectors to carry the FPGS gene, and thus express the FPGS gene product.

The present invention also provides an embodiment, whereby the FPGS drug activation system is combined with another established gene/prodrug activation system, such as ganciclovir/HSV-TK and 5-fluorocytosine/CD. FPGS gene therapy may also be combined with other established cancer therapeutic genes, including tumor suppressor genes, such as p53; apoptotic factors, such as bax, tumor necrosis factor alpha, and caspases; and cytokines, such as interleukin 2, interleukin 4, and interleukin 12.

In another embodiment of the present invention, the targetting specificity for FPGS gene delivery is facilitated by "transcriptional targeting," including the use of tumor-specific or tumor-selective DNA enhancer sequences. Examples of such sequences include those described for genes that encode tyrosinase (melanoma), ERBB2 (pancreatic cancer), carcinoembryonic antigen (lung and gastrointestinal cancer), DF3/MUC1 (breast cancer), alpha-fetoprotein (hepatoma), as well as synthetic gene regulation systems which allow for transcriptional control and other forms of regulated expression of the FPGS gene. Targeting also includes sequences that control expression of genes induced by hypoxia (hypoxia response elements), or other tumor-specific conditions and factors.

It is to be understood that both the foregoing general description and the following detailed description are exemplary and explanatory and are intended to provide further explanation of the invention as claimed.

BRIEF DESCRIPTION OF THE FIGURES

In FIG. 3A: over a wide range of concentrations—raw data points were fit to the sigmoidal dose-response curves shown using SigmaPlot 3.0. X-axis represents the log of the molar concentration of EDX. Standard errors were $\leq 8$ percent survival and are shown.

In FIG. 3B: using several doses in a narrower range (100–900 nM), corresponding to the region between log

Figure 3A:
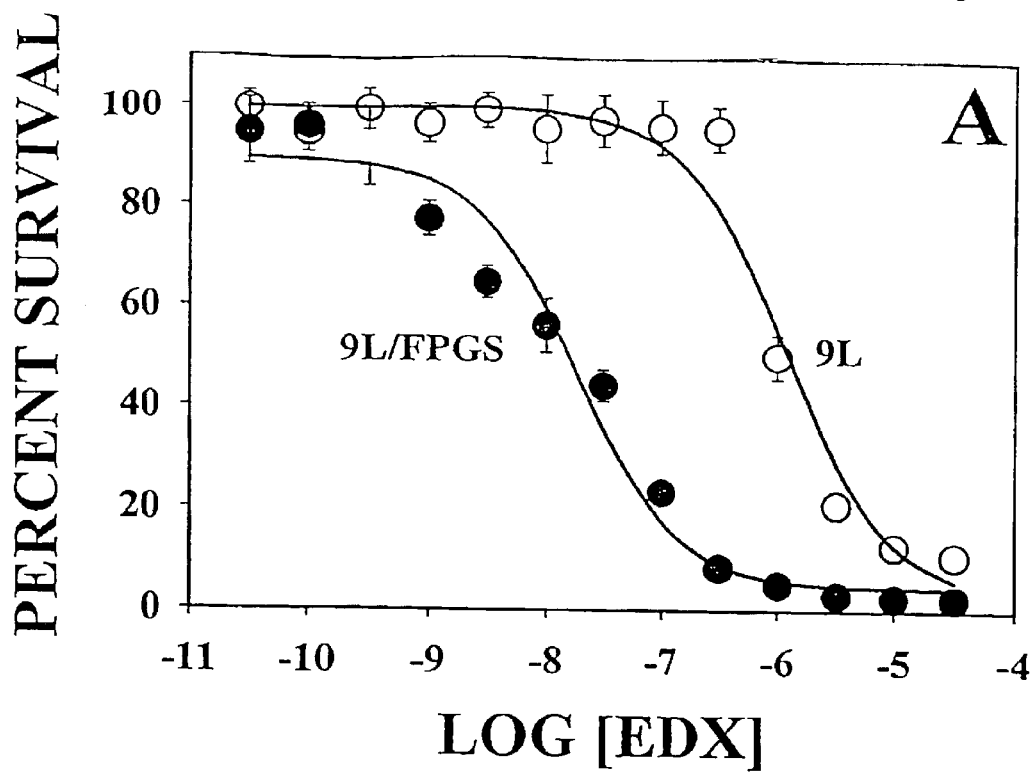
FIGS. 3A and 3B. EDX dose-response curves for 9L and 9L/FPGS cells in culture. Percent cell survival was determined for 9L (open circles) and 9L/FPGS (closed circles) cells plated in triplicate and treated with varying doses of EDX for 4 hours, followed by 3 days of growth in drug-free medium.

[EDX]=−7 to −6 in FIG. 3A. Standard errors were ≦3 percent cell survival and are thus too small to visualize.

Figure 4A:
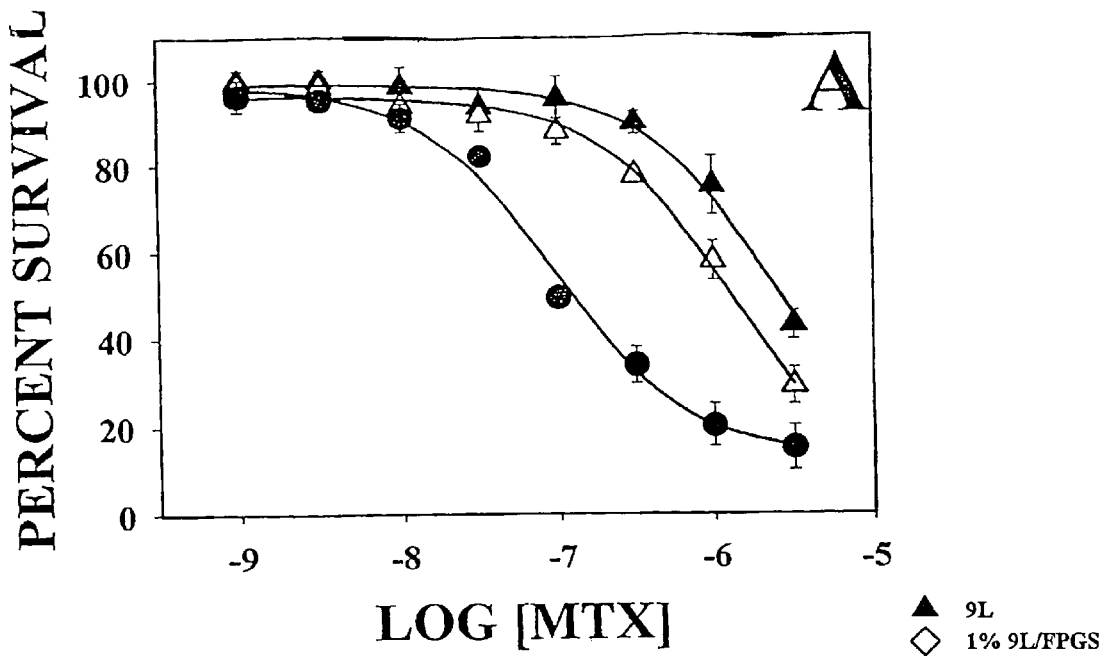
Figure 4B:
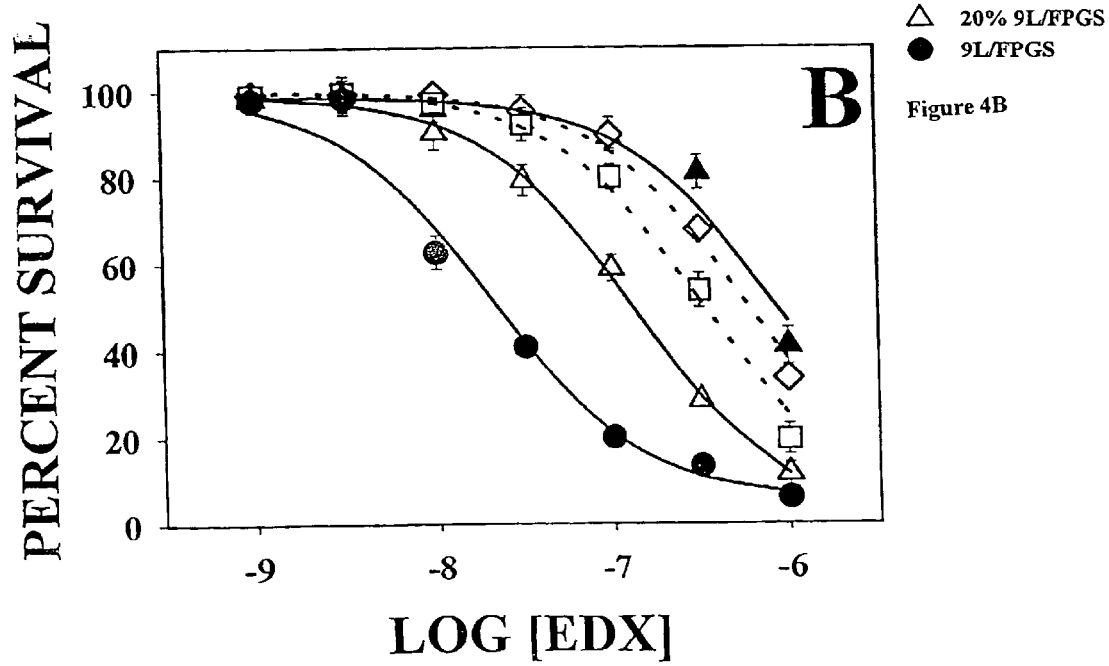

FIGS. 4A and 4B. The bystander effect of FPGS gene transfer. Data points for 9L (closed triangles), 9L/FPGS (closed circles), and a coculture containing 20% 9L/FPGS+ 80% 9L cells (open triangles) were fit to the sigmoidal dose-response curves (solid) shown using SigmaPlot 3.0. X-axis represents the log of the molar concentration of antifolate. Triplicate plates were treated with 4 hour pulses of MTX (FIG. 4A) or EDX (FIG. 4B), followed by 3 days of growth in drug-free medium. EDX pulses were also used to treat cocultures containing 10% 9L/FPGS cells (open squares) and 1% 9L/FPGS cells (open diamonds)—the sigmoidal curves (dashed) that fit these data points are also shown. Standard errors were ≦7 percent cell survival and are shown.

Figure 5:
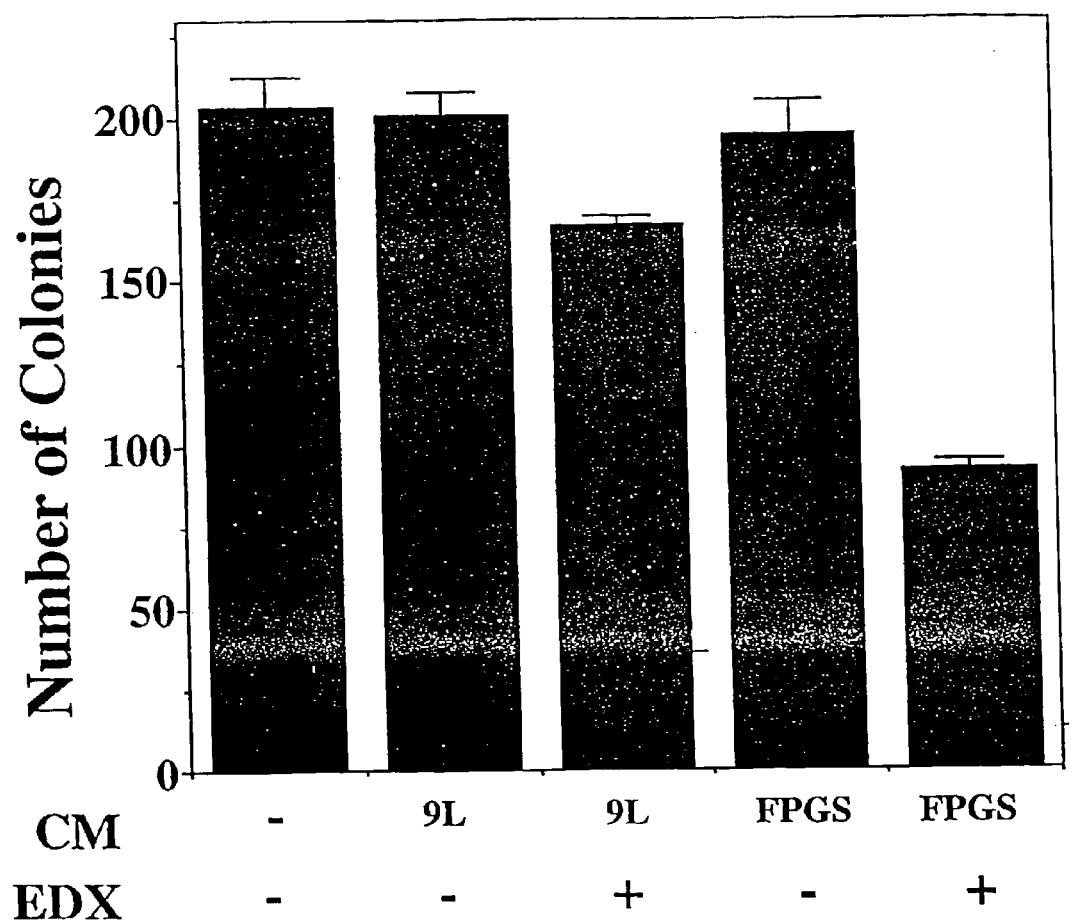

FIG. 5. Bystander effect is transmitted through the medium. X-gal positive colonies formed by triplicate plating of 1000 9L/BAG cells in conditioned medium (CM) were counted. The cell type (FPGS=9L/FPGS cells, negative sign=no CM used) from which the CM was taken are listed in the row labeled CM below the bar graph. In the row below that, a plus sign indicates that cells from which CM was taken were pulsed with 300 nM EDX during the first 4 hours of the 72 hours that the medium was conditioned. Number of colonies formed was significantly less when CM was from EDX-treated 9L/FPGS cells than it was when CM was from EDX-treated 9L cells (p<0.0005). Standard errors were ≦10 colonies and are shown.

Figure 6:
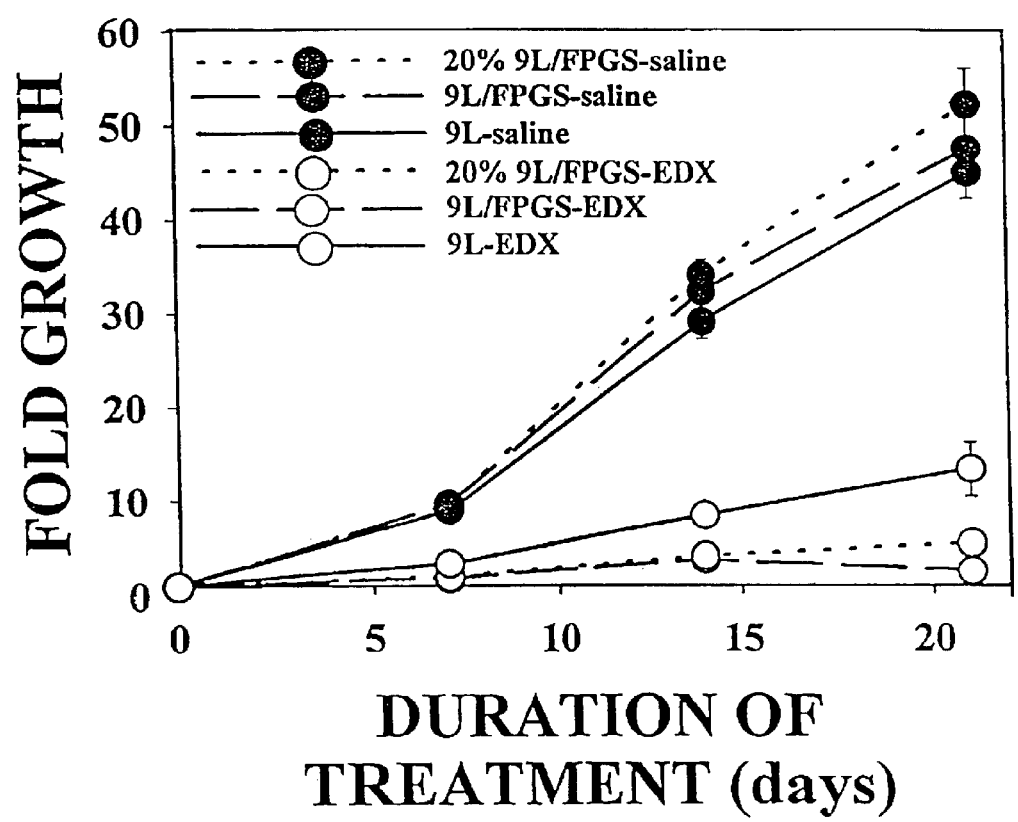

FIG. 6. Effect of EDX treatment on growth of subcutaneous 9L, 9L/FPGS, and mixed tumors. Subcutaneous tumors were formed by injecting 9L cells (solid line), 9L/FPGS cells (long dash), and a mixture of 20% 9L/FPGS cells+80% 9L cells (short dash) into the flanks of nude mice. Mice were treated daily with intraperitoneal injections of saline (solid circles) or 3 mg EDX/kg body weight (open circles). Standard errors were ≦5.5-fold growth and are shown. Saline-treated tumors achieved similar fold growth except after 3 weeks of treatment, when 20% 9L/FPGS tumors were slightly larger (p<0.05) than 9L tumors. EDX-treated 20% 9L/FPGS tumors never became significantly larger than EDX-treated 9L/FPGS tumors (p>0.05 at all 3 time points). EDX-treated 9L tumors were significantly larger (p<0.05) than EDX-treated 9L/FPGS and EDX-treated 20% 9L/FPGS tumors after two and three weeks of treatment.

DETAILED DESCRIPTION OF THE PREFERRED EMBODIMENTS

The present invention is directed to the killing of neoplastic cells using FPGS-based gene therapy in combination with an antifolate drug.

By "neoplastic cells" is intended cells whose normal growth control mechanisms are disrupted (typically by accumulated genetic mutations), thereby providing the potential for uncontrolled proliferation. The term is intended to include both benign and malignant neoplastic cells in both the central nervous system and the periphery. As used herein, the term "periphery" is intended to mean all other parts of the body outside of the brain or spinal cord.

For purposes of the invention, neoplastic cells include cells of tumors, neoplasms, carcinomas, sarcomas, papillomas, leukemias, lymphomas, and the like. The neoplastic cells can be malignant cells that are sensitive to antifolate chemotherapy, such as breast cancer and colon cancer. However, any neoplastic cell can be targeted since FPGS gene delivery will enhance the drug's anticancer effect. Thus, neoplastic cells, such as, e.g., central nervous system tumors (gliomas, astocytomas), lymphomas, lung cancer, melanoma, pancreatic cancer, ovarian cancer, prostate cancer, liver cancer, which are not conventionally treated with antifolate drugs, will be able to be targeted in the method of the invention.

By "FPGS gene" is intended a gene encoding the enzyme folylpolyglutamyl synthetase. By "activating an antifolate drug" is intended any metabolic reaction that increases the cytotoxic or cytostatic activity or otherwise increases the therapeutic efficacy of the antifolate drug; or that confers on the drug an additional mechanism of action beyond that which the drug exhibits in the absence of the metabolic reaction.

The FPGS gene may be from any species. FPGS cDNA from many species are known to those skilled in the art, and their nucleotide sequences can be obtained from the GenBank Sequence Database. The mammalian FPGS gene is preferred. The human FPGS gene is particularly preferred (see, GenBank accession number NM_004957; Garrow, T. A., et al., *Proc. Natl. Acad. Sci. USA* 89:9151–9155 (1992)).

The term "gene product" or "product of a particular gene" broadly refers to polypeptides or proteins encoded by a particular gene, but may also include transcription products of the particular gene.

By "chemotherapeutic agent that is activated by the product of said FPGS gene" is meant a pharmaceutical agent that can be used in the treatment of neoplasms, and that is capable of being activated by FPGS. By "activating" or "bioactivating" an antifolate drug is intended any metabolic reaction that increases the cytotoxic or cytostatic activity or otherwise increases the therapeutic efficacy of the drug; or that confers on the drug an additional mechanism of action beyond that which the agent exhibits in the absence of the metabolic reaction. By "cytotoxic" or "cytostatic" is intended causing or leading to cell death or slower tumor cell growth. Examples of antifolate drugs are MTX, EDX, aminopterin, and thymidylate synthetase inhibitors. Other antifolate drugs known to those skilled in the art can also be used in the present invention.

By "treating said neoplastic cells with a chemotherapeutic agent" is intended to include both the local delivery of the prodrug into or near the site of the tumor by, e.g., slow-release pellets, as well as the systemic administration of the chemotherapeutic agent, i. e., through intraperitoneal, intravenous, parenteral, or intramuscular routes. Localized delivery of the drug is expected to increase the fraction of the drug activated within the tumor, and thus increase drug efficacy.

Dosages of a particular chemotherapeutic agent may be administered according to current standard clinical practice. See, e.g., Hubbard, S. M. and Jenkins, J. F., "Chemotherapy Administration: Practical Guidelines" in *Cancer Chemotherapy: Principles and Practice*, Chabner and Collins, eds., J.B. Lippincott Company, Philadelphia, Pa. (1990), pages 449–463. Standard clinical practice may involve body surface area (BSA)-based dose calculations, as well as individualization of dosages based on pharmacokinetic optimization using plasma drug and metabolite concentrations ("therapeutic drug monitoring" or TDM). Such concentrations may be obtained using limited sampling or other pharmacokinetic sampling and modeling techniques (van Warmerdam, L. J., et al., *Neth J. Med.* 51:30–35 (1997); Desoize, B. and Robert, J., *Eur. J. Cancer* 30A:844–851 (1994); Gurney, H., *J. Clin. Oncol.* 14:2590–2611 (1996)).

Other factors, known to those skilled in the art, such as the clinical status and age of the patient, will also contribute to dosage adjustment.

The invention also provides preferred embodiments of the foregoing methods wherein the FPGS gene is the human FPGS gene and the chemotherapeutic agent is MTX.

The FPGS gene may be delivered to neoplastic cells using a viral vector, preferably one whose use for gene therapy is well known in the art. Techniques for the formation of vectors or virions are generally described in "Working Toward Human Gene Therapy," Chapter 28 in *Recombinant DNA*, 2nd Ed., Watson, J. D. et al., eds., New York: Scientific American Books, pp. 567–581 (1992). An overview of suitable viral vectors or virions is provided in Wilson, J. M., *Clin. Exp. Immunol.* 107(Suppl. 1):31–32 (1997), as well as Nakanishi, M., *Crit. Rev. Therapeu. Drug Carrier Systems* 12:263–310 (1995); Robbins, P. D., et al., *Trends Biotechnol.* 16:35–40 (1998); Zhang, J., et al., *Cancer Metastasis Rev.* 15:385–401 (1996); and Kramm, C. M., et al., *Brain Pathology* 5:345–381 (1995). Such vectors may be derived from viruses that contain RNA (Vile, R. G., et al., *Br. Med Bull.* 51:12–30 (1995)) or DNA (Ali M., et al., *Gene Ther.* 1:367–384 (1994)).

Examples of viral vector systems utilized in the gene therapy art include the following: retroviruses (Vile, R. G., supra; U.S. Pat. Nos. 5,741,486 and 5,763,242); adenoviruses (Brody, S. L., et al., *Ann. N.Y. Acad. Sci.* 716: 90–101 (1994); Heise, C. et al., *Nat. Med.* 3:639–645 (1997)); adenoviral/retroviral chimeras (Bilbao, G., et al., *FASEB J.* 11:624–634 (1997); Feng, M., et al., *Nat. Biotechnol.* 15:866–870 (1997)); adeno-associated viruses (Flotte, T. R. and Carter, B. J., *Gene Ther.* 2:357–362 (1995); U.S. Pat. No. 5,756,283); herpes simplex virus I or II (Latchman, D. S., *Mol. Biotechnol.* 2:179–195 (1994); U.S. Pat. No. 5,763, 217; Chase, M., et al., *Nature Biotechnol.* 16:444–448 (1998)); parvovirus (Shaughnessy, E., et al., *Semin Oncol.* 23:159–171 (1996)); reticuloendotheliosis virus (Donburg, R., *Gene Therap.* 2:301–310(1995)). Also of interest in the art, is the development of extrachromosomal replicating vectors for gene therapy (Calos, M. P., *Trends Genet.* 12:463–466 (1996)). Other viruses that can be used as vectors for gene delivery include poliovirus, papillomavirus, vaccinia virus, lentivirus, as well as hybrid or chimeric vectors incorporating favorable aspects of two or more viruses (Nakanishi, M., *Crit. Rev. Therapeu. Drug Carrier Systems* 12:263–310 (1995); Zhang, J., et al., *Cancer Metastasis Rev.* 15:385–401(1996); Jacoby, D. R., et al., *Gene Therapy* 4:1281–1283(1997)). Retroviruses, adenoviruses, and herpes viruses are the preferred viral vectors for gene delivery. Other suitable viral vectors will be readily apparent to the skilled artisan.

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan. Examples of enhancers include the tumor tissue-specific enhancers, described below.

Guidance in the construction of gene therapy vectors and the introduction thereof into affected animals for therapeutic purposes may be obtained in the above-referenced publications, as well as U.S. Pat. Nos. 5,631,236, 5,688,773, 5,691,177, 5,670,488, 5,529,774, 5,601,818, and WO 95/06486.

Generally, methods are known in the art for viral infection of the cells of interest. The virus can be injected into a patient bearing a neoplasm, either at, into, or near the site of neoplastic growth. Preferentially, the treatment will be by direct intraneoplastic inoculation. For tumors in the brain, magnetic resonance imaging (MRI), computerized tomography (CT), or other imaging guided stereotactic technique may be used to direct inoculation of the vector. The tumor may also be resected prior to treatment with the vectors of the invention.

The pharmaceutical compositions of the present invention would be advantageously administered in the form of injectable compositions. A typical composition for such purpose would comprise a pharmaceutically acceptable vehicle. Other pharmaceutically acceptable carriers include aqueous solutions, non-toxic excipients, including salts, preservatives, buffers and the like. See, *Remington's Pharmaceutical Sciences* (18th ed.), Mack Publishing Co. (1990). Examples of non-aqueous solvents are propylene glycol, polyethylene glycol, vegetable oil and injectable organic esters such as ethyloleate. Aqueous carriers include water, aqueous solutions, saline solutions, parenteral vehicles such as sodium chloride, Ringer's dextrose, etc. Intravenous vehicles include fluid and nutrient replenishers. The pH and exact concentration of the various components of the pharmaceutical composition are adjusted according to routine skills in the art (Goodman and Gilman, *The Pharmacological Basis for Therapeutics* (8th ed.) Pergamon Press (1990)).

Typically, the vector would be prepared as an injectable, either as liquid solutions or suspensions; solid forms suitable for solution in, or suspension in, liquid prior to injection may also be prepared. The preparation also may be emulsified. The active immunogenic ingredient is often mixed with an excipient which is pharmaceutically-acceptable and compatible with the active ingredient. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators.

In general, the virus is provided in a therapeutically effective amount to infect and kill target cells. The quantity of the vector to be administered, both according to number of treatments and amount, will also depend on factors such as the clinical status, age, and weight of the subject to be treated, the capacity of the subject's immune system to synthesize antibodies, and available volume. Precise amounts of active ingredient required to be administered depend on the judgment of the gene therapist and will be particular to each individual patient. Generally, the viral vector is administered in titers ranging from about $1\times10^5$ to about $1\times10^9$ colony forming units (cfu) per ml, although ranges may vary. Preferred titers will range from about $1\times10^6$ to about $1\times10^8$ cfu/ml.

In one embodiment, a packaging cell line is transduced with a retroviral vector carrying the FPGS gene to form a producer cell line. The packaging cells may be transduced by any means known in the art, including, e.g., electroporation, $CaPO_4$ precipitation, or the use of liposomes. Examples of packaging cells that may be transfected include, but are not limited to, BOSC23, Bing, PE501, PA317, Ψ-2, Ψ-AM, PA12, T19-14X, VT-19-17-H2, Ψ-CRE, Ψ-CRIP, GP+E86, GP+envAm12, and DAN cell lines. Guidance on retroviral producing packaging cells and how to construct them can be found in Short et al., *J. Neurosci. Res.* 27:427–433 (1990); Miller, A. D., *Human Gene Ther.* 1:5–14 (1990); Danos, O, "Construction of Retroviral Packaging Cell Lines," in Methods in Molecular Biology (M. Collins, ed.), Vol. 8, The Humana Press Inc., Clifton, N.J., 17–26 (1991); Murdoch, B., et al., *Gene Therapy* 4:744–749 (1997); and U.S. Pat. Nos. 5,529,774, which issued on Jun. 25, 1996 and 5,591,624, which issued on Jan. 7, 1997.

Retroviral vectors have also been successfully packaged with a vesicular stomatitis virus (VSV) envelope glycoprotein G ("pseudotyping"). These vectors are more stable and can be concentrated to $10^9$ cfu/ml, allowing them to be injected directly (Burns, J. C., et al., *Proc. Natl. Acad. Sci. USA* 90:8033–8037 (1993)).

The producer cells can then be grafted near or into the tumor in an amount effective to inhibit or kill the neoplastic cells. Direct injection of high titer retroviral producer cells (Murdoch, B., et al., *Gene Ther.* 4:744–749 (1997); Onodera, M., et al., *Hum Gene Ther.* 8:1189–1194 (1997)) should allow for efficient in situ infection with the retroviral sequences (Rainov, N. G., et al., *Cancer Gene Ther.* 3:99–106 (1996); Ram, Z., et al., *Cancer Res.* 53:83–88 (1993)). Producer cells injected intratumorally do not generally migrate from the site of injection. Moreover, although they may be rejected by the host, this does not occur for 5–10 days, by which time retroviral infection of nearby tumor cells will have occurred (Ram, Z., et al., *J. Neurosurg.* 79:400–407 (1993)). In general, vector producer cell (VPC) dosages range from about $2.5 \times 10^8$ VPCs to about $1 \times 10^9$ VPCs. The exact amount of producer cells will ultimately be determined by the skilled artisan based on numerous factors, including, but not limited to, the available injectable volume, clinical status of the patient, and tumor type and size.

Preferably, the viral genomes of the viral vectors used in the invention should be modified to remove or limit their ability to replicate, however, replication conditional viruses will also be useful in the present invention, as will replicating vectors that are capable of targeting certain cells. See, e.g., Zhang, J., et al., *Cancer Metastasis Rev.* 15:385–401 (1996). Chase, M., et al. (*Nature Biotechnol.* 16:444–448 (1998)) used a herpes virus with an inactivated viral ribonucleotide reductase gene that selectively delivered P450 2B 1 to tumor cells that overexpress the mammalian ribonucleotide reductase enzyme, which is required for this modified virus to replicate.

The FPGS gene can also be delivered using non-viral methods for gene transfer, preferably those whose use in gene therapy is known in the art (Nakanishi, M., *Crit. Rev. Therapeu. Drug Carrier Systems* 12:263–310 (1995); Abdallah, B., et al., *Biol. Cell* 85:1–7 (1995); Zhang, J., et al., *Cancer Metastasis Rev.* 15:385–401(1996); Philips, S. C., *Biologicals* 23:13–16(1995); Lee, R. J. and Huang, L., *Crit. Rev. Ther. Drug Carrier Syst.* 14:173–206 (1997)). Examples of such non-viral vectors for gene delivery include prokaryotic vectors, such as tumor targeted bacterial vectors (Pawelek, J. M., et al., *Cancer Res.* 57:4537–4544 (1997)), cationic liposomes, DNA-protein complexes, non-viral T7 autogene vectors (Chen, X., et al., *Hum. Gene Ther.* 9:729–736 (1998)), fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburst polyamidoamine dendrimers (Kukowska-Latallo, J. F., et al., *Proc Natl Acad Sci USA* 93:4897–4902 (1996); Tang, M. X., et al., *Bioconjug. Chem.* 7:703–714 (1996)), cationic peptides (Wyman, T. B., et al., *Biochemistry* 36:3008–3017 (1997)), and mammalian artificial chromosomes (Ascenzioni, F., et al., *Cancer Lett.* 118:135–142 (1997)).

In addition, the present invention provides an embodiment of the foregoing methods wherein the FPGS gene is delivered using any cellular vector, preferably one whose use for gene therapy is well-established for those skilled in the art. Examples of such cellular vectors for gene therapy include endothelial cells (Rancourt, C., et al., *Clin. Cancer Res.* 4:265–270(1998); Ojeifo, J. O., et al., *Cytokines Mol. Ther.* 2:89–101 (1996)) and macrophages including tumor-infiltrating macrophages (Zufferey, R, et al., *Nat. Biotechnol.* 15:871–875 (1997); Naldini, L., et al., *Science* 272:263–267 (1996)), each of which may be modified using viral or non-viral vectors to carry the FPGS gene, and thus express the FPGS gene products. Other suitable non-viral vectors will be readily apparent to the skilled artisan.

In another embodiment of the invention, the FPGS-based drug activation system is combined with established gene/prodrug activation systems, including ganciclovir/HSV-TK and 5-fluorocytosine/CD (Moolten, F. L., *Cancer Gene Therapy* 1:279–287(1994)). This can be accomplished either by separate transfer of both suicide genes (Aghi, M., et al., *J. Natl. Cancer Inst.* 90:370–380 (1998); Uckert, W., et al., *Human Gene Therapy* 9:855–865(1998)), or by transfer of a fusion gene encoding both drug activation enzymes (Rogulski, K. R., et al., *Human Gene Therapy* 8:73–85 (1997)). FPGS gene therapy may also be combined with other established cancer therapeutic genes, including tumor suppressor genes, such as p53 (Roth, J. A., et al., *Nature Med.* 2:985–991 (1996); Harris, M. P., et al., *Cancer Gene Therap.* 3:121–130 (1996)); apoptotic factors, such as bax (Bargou, R. C., et al., *J. Clin. Invest.* 97:2651–2659 (1996)), tumor necrosis factor alpha (Gillio, T. A., et al., *Blood* 87:2486–2495 (1996)), and caspases (Kondo, S., et al., *Cancer Research* 58:962–967(1998); Yu, J. S., et al., *Cancer Research* 56:5423–5427 (1996)); and cytokines, such as interleukin 2 (Clary, B. M., et al., *Cancer Gene Ther.* 4:97–104 (1997); O'Malley, B. W., et al., *Ann. N.Y. Acad. Sci.* 842:163–170 (1998)), interleukin 4 (Benedetti, S., et al., *Human Gene Therapy* 8:1345–1353 (1997)), and interleukin 12 (Chen, L., et al., *Immunol.* 159:351–359 (1997)).

In an additional embodiment, the targetting specificity for FPGS gene delivery may be facilitated by targeted delivery or targeted expression ("transcriptional targeting"), including the use of tumor-specific or tumor-selective DNA enhancer sequences to selectively activate expression of the transduced gene in the tumor cell at either the primary tumor site or its metastases (Miller, N. and Whelan, J., *Hum. Gene Ther.* 8:803–815 (1997); Walther, W. and Stein, U., *J. Mol. Med.* 74:379–392 (1996); Schnierle, B. S. and Groner, B., *Gene Therapy* 3:1069–1073 (1996); Lan, K-H., et al., *Cancer Res.* 57:4279–4284 (1997)); Dachs, G. U., et al., *Oncol. Res.* 9:313–325 (1997)). Examples of this approach include those DNA enhancers that have been derived from genes that encode tyrosinase (allowing for targeting to melanoma), ERBB2 (targeting to pancreatic cancer), carcinoembryonic antigen (targeting to lung and gastrointestinal malignancies, including colon, pancreatic and gastric cancer), DF3/MUC1 (targeting to breast cancer), and alpha-fetoprotein (targeting to hepatoma). The use of synthetic gene regulation systems, which allow for transcriptional control and other forms of regulated expression of the FPGS gene, may also be used (Miller, N. and Whelan, J., *Hum. Gene Ther.* 8:803–815 (1997); Vile, R. G., *Semin. Cancer Biol.* 5:429–436 (1994); Hwang, J. J., et al., *J. Virol.* 70:8138–8141 (1996); Massie, B., et al., *J. Virol.* 72:2289–2296 (1998)).

Another possibility is the use of DNA regulatory elements that are controlled by tumor-specific conditions and factors. For example, one unique aspect of solid tumors is their localized hypoxic environment (Brown, J. M. and Giaccia, A. J., *Cancer Res.* 58:1408–1416 (1998)). This characteristic can be exploited to induce the expression of genes that are controlled by hypoxia (hypoxia response elements or "HRE") (Dachs, G. U., et al., *Nature Med.* 3:515–520 (1997); O'Rourke, J. F., et al., *Oncol. Res.* 9: 327–332 (1997)). Thus, in an additional embodiment, HRE sequences can be used for the transcriptional targeting of FPGS genes to hypoxic neoplastic cells.

Exemplary candidates for treatment according to the present invention include, but are not limited to humans, other mammals, or non-mammal animals suffering from neoplasms, and in particular, malignant tumors of the central nervous system.

As a result of the enhanced production of cytotoxic drug metabolites that occurs when a FPGS gene is transferred to tumor cells, the method of the invention allows for greater localized tumor toxicity at a given drug concentration, leading to an enhanced chemotherapeutic response. It may also allow for lower doses of the drug to be given, thereby reducing toxic effects to the patient by decreasing exposure of normal cells and tissues to cytotoxic metabolites.

The present invention is further illustrated by the following examples. These examples are provided to aid in the understanding of the invention and are not construed as a limitation thereof.

EXAMPLE 1

Materials and Methods

Chemicals: Amethopterin (methotrexate or MTX) and aminopterin were obtained from Sigma Biochemical (St. Louis, Mo.). Edatrexate (EDX) was provided by Dr. F. M. Sirotnak (Memorial Sloan-Kettering Cancer Center, New York, N.Y.). The non-polyglutamylatable antifolate PT523 (Nα-4amino-4-deoxypteroyl-N-δ-hemiphthaloyl-L-omithine, Rosowsky, A., et al., *Journal of Medicinal Chemistry* 31:1332–1337 (1988)) and methotrexate polyglutamate standards MTX-G1 to MTX-G5 (NMT itself has one glutamate, MTX-G1 through MTX-G5 represent MTX polyglutamates with one to five additional glutamates attached) were provided by Dr. J. Wright (Dana Farber Cancer Institute, Boston, Mass.).

Expression Plasmids: The human FPGS cDNA was provided by Dr. B. Shane (University of California, Berkeley) (Garrow, T. A., et al., *Proc. Natl. Acad. Sci. USA* 89:9151–9155 (1992)). This cDNA was cloned into the plasmid pCDNA3.1 (Invitrogen Co., Carlsbad, Calif.), where it could be expressed under control of the CMV promoter, while the gene for neomycin resistance would be expressed under control of the SV40 promoter.

Tissue and Cell Lines: Glioblastoma and astrocytoma tissue were obtained from Dr. D. Louis (Massachusetts General Hospital; Boston, Mass.); normal liver and liver tissue containing colon carcinoma metastases were obtained from Dr. K. Tanabe (Massachusetts General Hospital; Boston, Mass.). All cell lines were grown at 37° C. in a 5% $CO_2$-95% air atmosphere in Dulbecco's modified Eagle medium (Sigma) containing 10% fetal bovine serum (Sigma), 100 U/mL. penicillin, and 100 μg/mL streptomycin (Sigma). The rat 9L gliosarcoma cell line has been described previously (Weizsaecker, M., et al., *Journal of Neurology* 224:183–192 (1981)). The transfectant 9L/FPGS was generated by lipofectamine-mediated (Life Technologies Inc., GIBCO BRL; Gaithersburg, Md.) transfection of 9L cells with the plasmid pCDNA3.1 containing the human FPGS cDNA and was cloned under selection in medium containing 1 mg/mL G418 (neomycin analogue; Life Technologies, Inc.). The cell line 9L/BAG expresses the histochemically detectable marker β-galactosidase (LacZ) due to infection with the BAG retrovirus (Scharf, J. M., et al., *Transgenics* 1:219–224 (1994)). The human glioma cell line U87MG was purchased from American Tissue Culture Collection (Ponten, J., Macintyre, E. H., *Acta Pathol Microbiol Scand* 74:465–486 (1968)).

Cell Culture Survival Studies: Cells were plated in triplicate at $8 \times 10^5$ cells per 10-cm-diameter plate, and were allowed to adhere for 4 hours, after which the medium was replaced with medium containing MTX or EDX. After 4 hours drug exposure, the plates were washed three times with 4 mL PBS. Drug-free medium was then added, and three days later the cells were trypsinized and counted on a model ZM Coulter apparatus. Dose-response curves were generated using Sigma Plot 3.0, which employs curve-fitting parameters based on the Marquardt-Levenberg method (Marquardt, D. W., Siam, J., *J. Soc. Indust. Appl. Math* 11:431–441 (1963)).

For bystander effect studies, cells were plated in triplicate with varying combinations of 9L/FPGS and 9L cells such that the total number of cells was $8 \times 10^5$ per 10-cm-diameter plate. The same protocol of 4 hour cell adherence followed by 4 hour drug exposure, washes, growth in drug free medium for 3 days, and counting on a ZM coulter apparatus was then followed. In an additional series of experiments, conditioned medium was harvested from untreated 9L and 9L/FPGS cells and from 9L and 9L/FPGS cells that had been pulsed with 0.3 μM EDX for 4 hours followed by 3 days of growth in drug-free medium. Four mL conditioned medium+2 mL fresh medium were added to 10-cm-diameter plates containing 9L/BAG cells plated overnight (1000 cells/dish, with a clonogenic efficiency of approximately 20%). Six days later, the cells were fixed with 4% paraformaldehyde in PBS. Fixed cells were stained for LacZ by incubating overnight in a solution containing 35 mM potassium ferricyanide, 35 mM potassium ferrocyanide, 2 mM magnesium chloride, and 0.2% 5-bromo-4-chloro-3-indolyl-β-D galactoside (Xgal; Fisher Scientific Co.;Pittsburgh, Pa.) at pH=7.3 (Price, J., et al., *Proceedings of the National Academy of Sciences USA* 84:156–160 (1987)). The next day, blue colonies greater than 1 mm in diameter were counted.

Enzymatic Assay: FPGS activity was measured using a modification of a previously described protocol (Egan, M. G., et al., *Journal of Biological Chemistry* 270:5462–5468 (1995)). Cells were trypsinized; suspended in 25 mM Tris-HCl (pH 7.5), 5 mM 2-mercaptoethanol, 2 μg/mL aprotinin (Sigma), 1 μg/mL leupeptin (Sigma); and sonicated for 15 sec: at half maximal power (550 Sonic Dismembrator; Fisher). Sonicated cells were centrifuged to remove cellular debris at 10,000×g for 2 min at 4° C. Protein concentration was calculated using the Bradford protein assay (Bio-Rad Laboratories; Hercules, Calif.). Frozen tissue was ground into small pieces using a mortar and pestle, suspended in lysis buffer (50 mM Tris pH 7.4, 250 mM NaCl, 0.1% NP40, 5 mM EDTA, 2 μg/mL aprotinin, 1 μg/mL leupeptin), homogenized (Brinkmann Instruments Co.; Westbury, N.Y.), and kept on ice for one hour to allow for completion of lysis. To detect the low FPGS activity in tissue, the samples were concentrated using an Integrated Speed Vac system (Savant Instruments Inc.; Farmingdale, N.Y.), after which protein concentration was determined using the Bradford assay. The FPGS enzymatic assay reaction mixture consisted of 1 M Tris (pH 9.75), 50 mM glycine, 100 μM aminopterin, 1 mM glutamate, 50 μM [$^3$H] glutamate (1 μCi/μL; 50 Ci/mmol; DuPont New England Nuclear;

Boston, Mass.), 5 mM ATP, 10 mM $MgCl_2$, 20 mM KCl, 100 mM 2-mercaptoethanol, 0.1 µg/µl BSA, and 0.4 to 0.8 mg cellular protein. Reaction was carried out in 500 µL at 37° C. for 2 hours, and was terminated by adding 1.5 mL ice-cold 30 mM 2-mercaptoethanol, 10 mM glutamate. Free glutamate was separated from glutamate bound to aminopterin by chromatography on a 1–1.5 mL bed volume minicolumn (Poly-Prep Chromatography Column, Bio-Rad) containing. DE52 Diethylaminoethyl (DEAE) cellulose (Whatman). The column was equilibrated with 5 mL 10 mM Tris (pH 7.5), 80 mM NaCl. The terminated reaction was then applied to the column. The column was washed with 5 mL equilibration buffer to remove unincorporated glutamate. The glutamylated aminopterin was then eluted with 3 mL 0.1 N HCl with the eluant collected in a scintillation vial containing 10 mL scintillation fluid (ScintiVerse II, Fisher), and subsequently counted on a scintillation counter.

Thin Layer Chromatography of MTX Metabolites: $10^6$ 9L or 9L/FPGS cells were plated in 6-cm diameter dishes and allowed to adhere for 4 hours, after which cells were incubated overnight with 2 µM 3', 5', 7-[$^3$H] methotrexate (Moravek Biochemicals; Brea, Calif.). Cells were then trypsinized, centrifuged, resuspended in 300 µL deionized water, and sonicated for 45 seconds at half-maximal power. Sonicated cells were centrifuged briefly to remove cellular debris, after which protein concentration was calculated using the Bradford protein assay. Proteins were precipitated with 1 mL methanol at −20° C. for 2 hr. Precipitated proteins were removed by centrifugation at 20,000 g for 30 min, and the supernatant was then concentrated to 30 µL under a stream of $N_2$ at 37° C. on a Meyer N-Evap Analytical Evaporator (Organomation Associates Inc., Northborough, Mass.). A 1 µL aliquot was scintillation counted—cpm were converted into moles of drug taken up by determining the cpm of a known quantity of [$^3$H] MTX. MTX polyglutamates were separated by ascending thin layer chromatography (TLC) of samples on Baker Si250PA silica gel plates (Fisher), as described previously (Wright, J. E., et al., *Biochemical Pharmacology* 36:2209–2214 (1987); Ellenberger, T. E., et al., *Journal of Biological Chemistry* 264:15960–15966 (1989)). Plates were eluted with a chloroforrn-methanol-acetic acid mixture (2:2:1) containing 20 mg/mL cetyl trimethylammonium bromide (Sigma). Following elution, the plates were placed under ordinary fluorescent light for 2 days, after which 20 nmol unlabelled standards were visualized under long-wave ultraviolet light. Plates were run in duplicate and the average $R_F$ values of the standards were: MTX=0.66; MTX-G1=0.59; MTX-G2=0.44, MTX-G3=0.33; MTX-G4=0.27; MTX-G5=0.25. Regions corresponding to where standards migrated were marked in the sample lane, scraped individually into scintillation vials, and counted. The amount of each radioactive metabolite in a sample lane was determined as a percentage of the total radioactivity recovered from that sample lane, after subtraction of the background counts obtained from lanes lacking radioactive sample.

In Vivo Experiments: $10^5$ 9L or 9L/FPGS cells or a mixture of $8×10^5$ 9L+$2×10^5$ 9L/FPGS cells in 200 µL DMEM were injected subcutaneously into the flanks of six week old female nude mice (NCr/Sed, nu/nu, 20 gm; Massachusetts General Hospital breeding colony). After 14 days, when the tumors had reached an average volume of 60 $mm^3$, the mice were randomly divided into experimental groups with five mice per group. Intraperitoneal injections of varying MTX or EDX doses dissolved in 200 µL 0.9% NaCl were administered either daily or every third day. Tumor size was measured weekly using calipers. Tumor volume was calculated as length×width×height, as described previously (Takamiya, Y., et al., *Journal of Neuroscience Research* 33:493–503 (1992)).

Results

Characterization of Glioma FPGS Activity

Gliomas have been used in numerous cancer gene therapy studies, but before using gliomas in this study of FPGS gene delivery, it was important to determine if their FPGS activities were low enough that they could potentially experience enhanced antifolate sensitivity upon transfection (Roth, J. A., Cristiano, R. J., *Journal of the National Cancer Institute* 89:21–39 (1997); Aghi, M., et al., *Journal of the National Cancer Institute* 90:370–380 (1998)). Cell lines derived from tumor tissue frequently have a higher replication fraction and rate than the primary tumor since rapidly dividing cells are selected for over time. Since increased proliferation rate is associated with increased FPGS activity, a cell line's FPGS activity is generally higher than that of the tumor from which it was derived (Barredo, J., Moran, R. G., *Molecular Pharmacology* 42:687–694 (1992)). Therefore, the first step in this study was to calculate the FPGS activity of human glioblastoma multiforme (GBM) and astrocytoma tissues. These activities were 32 pmol aminopterin polyglutamates formcd/mg protein/hour (GBM) and 36 pmol/mg protein/hour (astrocytoma), almost 10-fold less than the 323 pmol/mg protein/hour (Table 1) found in human liver tissue containing colon carcinoma metastases, a type of tumor which has been described as having relatively high FPGS activity (Peters, G. J., *Advances in Experimental Medicine and Biology* 338:651–654 (1993)). The FPGS activities of the 9L (rat) and U87 (human) glioma cell lines were then determined. U87 cells polyglutamylated 540 pmol aminopterin/hr/mg protein, slightly more than the 360 pmol/hr/mg protein polyglutamylated by 9L cells (Table 1).

TABLE 1

FPGS Activities of Cell Lines and Tissues Using Aminopterin as a Substrate

| SOURCE | FPGS ACTIVITY[a] (pmol aminopterin glutamylated/hr/mg protein) |
| --- | --- |
| U87 human cell line | 540 ± 66 |
| 9L rat cell line | 360 ± 40 |
| 9L/FPGS rat cell line | 1630 ± 102 |
| human glioblastoma tissue | 32 ± 3 |
| human astrocytoma tissue | 36 ± 4 |
| normal human liver tissue | 185 ± 13 |
| human liver tissue with colon cancer mestastases | 323 ± 17 |

[a]Samples were processed as described in "Materials and Methods" and were evaluated in triplicate at three different protein concentrations to confirm a linear relationship between enzymatic activity and protein concentration. Standard errors are shown.

Transfection of 9L with FPGS cDNA and Selection of Clones

In order to evaluate the effect of increased FPGS activity on MTX sensitivity, 9L cells were transfected with a plasmid containing the human FPGS cDNA under the control of the cytomegalovirus (CMV) immediate early gene promoter, as well as a gene conferring neomycin resistance. The parental cell line and 16G418-resistant clones selected after transfection were treated with 0.3 µM MTX for 4 hours, followed by 3 days of growth in drug-free medium. Susceptibility to 4 hour MTX pulses correlates somewhat with FPGS activity (Kim, J. S., et al., *Journal of Biological Chemistry*

268:21680–21685 (1993)). Fourteen clones displayed approximately the 90% survival seen with 9L cells, but two clones each displayed approximately 40% survival in response to the pulse. One of these clones was selected for further study and designated 9L/FPGS.

The FPGS activity of 9L/FPGS cells was 1630 pmol aminopterin polyglutamylated/mg protein/hour (Table 1), a more than 4-fold increase over the FPGS activity of the parental 9L cell line. The G418-resistant clone whose MTX pulse survival was comparable to 9L/FPGS possessed FPGS activity comparable to 9L/FPGS; while a G418-resistant clone whose MTX pulse survival was comparable to 9L possessed FPGS activity comparable to 9L (data not shown). Further evidence that the enhanced MTX pulse susceptibility of 9L/FPGS resulted from increased FPGS enzyme activity was offered by the fact that 9L and 9L/FPGS cells displayed similar sensitivity to 4 hour pulses of the non-polyglutamylatable antifolate PT523 (Rosowsky, A., et al., *Journal of Medicinal Chemistry* 31:1332–1337(1988)). In addition, 9L and 9L/FPGS cells proliferated at comparable rates in the absence of MTX. Thus, the enhanced FPGS activity of 9L/FPGS cells did not affect their growth rate, nor did 9L/FPGS cells possess an altered replication rate arising through clonal variation.

Quantificaton of MTX Polyglutamates Formed by 9L and 9L/FPGS

The FPGS enzyme assay measures the amount of drug converted into any of the five polyglutamates. But, the attachment of each glutamate to the drug by FPGS has different enzyme kinetics. And, it is only after attachment of the last three glutamate residues that the drug's retention time and inhibitory properties improve substantially (Chu, E. and Allegra, C, Antifolates," in *Cancer Chemotherapy and Biotherapy: Principles and Practice*, Chabner et al, eds., Lippincott-Raven, Philadelphia (I996), pp. 109–148). Thus, it is important to determine a cell line's capacity to form each of the MTX polyglutamates. In order to examine the capacity of 9L and 9L/FPGS to synthesize the different MTX polyglutamates, thin layer chromatography (TLC) was used to separate the MTX polyglutamates. 9L and 9L/FPGS cells were incubated with 2 $\mu$M [$^3$H] MTX for 24 hr, and the total incorporation of radioactivity was measured. MTX levels were 6.3 and 12.7 pmol/mg protein in 9L and 9L/FPGS cells, respectively, indicating that 9L/FPGS cells retain twice as much MTX as 9L cells after a 24 hour exposure. Next, the different polyglutamates formed after 24 hours of exposure to [$^3$H] MTX were resolved using TLC. Thirty percent of the total radioactivity in 9L cell represented MTX unaltered by FPGS, compared to only 10% of the total radioactivity in 9L/FPGS extracts (Table 2). Only 14% of the total radioactivity in 9L extracts was associated with the higher order polyglutamates MTX-G4 and G5, compared to 31% of the total radioactivity in 9L/FPGS extracts (Table 2). These results indicate that the higher FPGS enzyme activity of 9L/FPGS cells is indeed associated with greater formation of the higher order MAX polyglutamates, This greater formation of higher order polyglutamates in 9L/FPGS cells leads to greater cellular uptake of MTX. The greater capacity of 9L/FPGS cells to convert MTX into the highly retained polyglutamates lowers the intracellular concentration of monoglutamylated MTX, making MTX influx more favorable than efflux.

TABLE 2

Metabolism of MTX and 9L and 9L/FPGS After 24 hour Exposure to 2 $\mu$M MTX

| CELL LINE | TOTAL MTX ACCUMULATED (pmol/mg protein)[a] | POLYGLUTAMATE DISTRIBUTION (percentages)[b] | | | | | |
|---|---|---|---|---|---|---|---|
| | | MTX | MTX-G1 | MTX-G2 | MTX-G3 | MTX-G4 | MTX-G5 |
| 9L | 6.3 | 30 | 29 | 15 | 13 | 13 | 1 |
| 9L/FPGS | 12.7 | 10 | 22 | 19 | 18 | 28 | 3 |

[a]After treating 9L and 9L/FPGS cells for 24 hours with [$^3$H] MTX, cells were lysed and total cellular uptake of radioactivity was determined and converted into total MTX accumulated using the cpm found in a known quantity of [$^3$H] MTX.
[b]Lysates were run on TLC plates in duplicate, along with MTX polyglutamate standards. Following elution, polyglutamate standards were visualized under ultraviolet light. In the sample lanes, the positions corresponding to the polyglutamate standards were scraped into scintillation vials and counted to determine radioactivity. Percentages shown represent percentages of total sample lane radioactivity found in each polyglutamate's position.

Dose-response Curves for 9L and 9L/FPGS Cells Treated with Four Hour MTX Pulses

Figure 1:
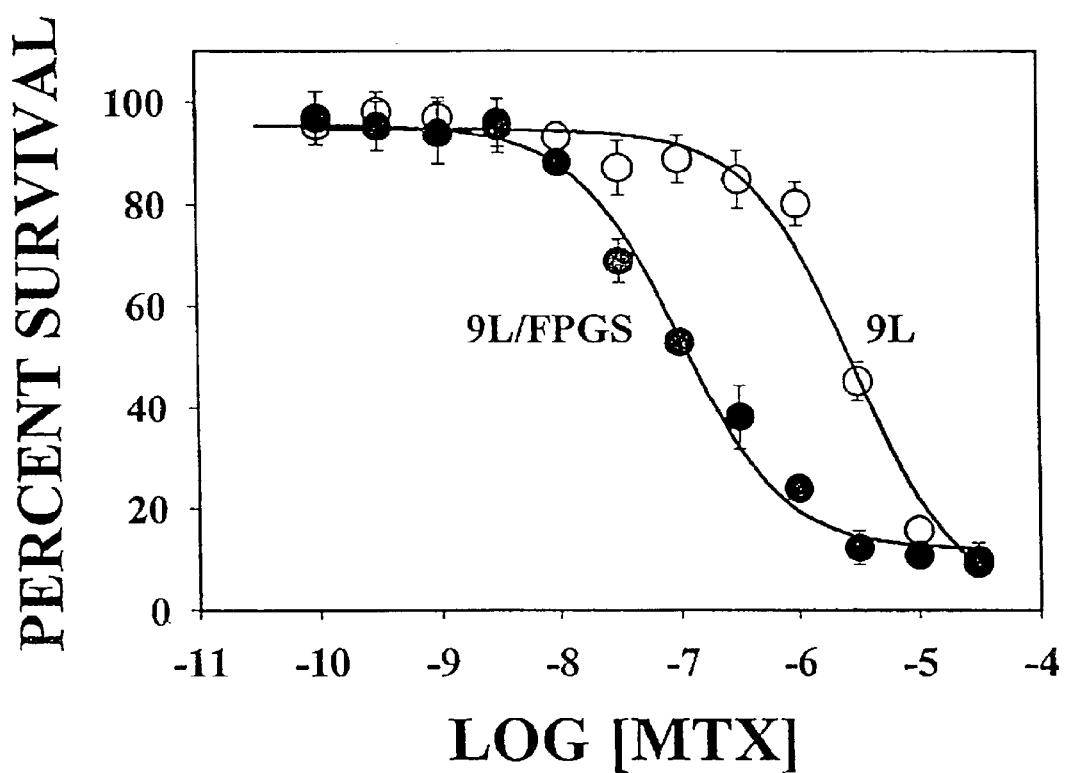
FIG. 1. MTX dose-response curves for 9L and 9L/FPGS cells in culture. Percent cell survival was determined for 9L (open circles) and 9L/FPGS (closed circles) cells treated with varying doses of MTX for 4 hours, followed by 3 days of growth in drug-free medium. The x-axis represents the log of the molar concentration of MTX. Raw data points represent the averages of triplicate platings and were fit to the sigmoidal dose-response curves shown using SigmaPlot 3.0. Standard errors were $\leq 6.3\%$ cell survival and are shown.

To further characterize the cell lines, the percent survivals of 9L and 9L/FPGS cells after treatment with 4 hour pulses of varying MTX doses were measured (FIG. 1). A statistically significant (p<0.01) difference in sensitivity to 4 hour MAC pulses between the two cell lines existed over a 100-fold range of MTX doses (30 nM–3 $\mu$M). The raw data points were then fit to sigmoidal dose-response curves (FIG. 1), which were used to obtain ED$_{50}$ (drug concentration that reduces cell number by 50%) values of 2.9 $\mu$M for 9L and 101 nM for 9L/FPGS (Table 3), a 29-fold difference. The ED$_{50}$ for cells grown in the presence of MTX for 72 hours was 40 nM for both 9L and 9L/FPGS cells (dose-response curves not shown). Thus, 9L/FPGS cells display enhanced MTX sensitivity when exposed to the drug for brief periods.

TABLE 3

Dose-Response Parameters for Antifolate Treatment of Cultured Glioma Cells

| CELL LINE | DURATION OF DRUG EXPOSURE | DRUG | ED$_{50}$[a] |
|---|---|---|---|
| 9L | 72 hrs | MTX | 40 nM |
| 9L/FPGS | 72 hrs | MTX | 40 nM |
| U87 | 4 hrs | MTX | 30 $\mu$M |
| 9L | 4 hrs | MTX | 2.9 $\mu$M |
| 9L/FPGS | 4 hrs | MTX | 101 nM[b] |
| 9L | 4 hrs | EDX | 1.2 $\mu$M |
| 9L/FPGS | 4 hrs | EDX | 18 nM[c] |
| 9L | 4 hrs | MTX | 2.7 $\mu$M |
| 20% 9LFPGS[d] | 4 hrs | MTX | 1.4 $\mu$M |
| 9L/FPGS | 4 hrs | MTX | 93 nM[e] |
| 9L | 4 hrs | EDX | 895 nM |

TABLE 3-continued

Dose-Response Parameters for Antifolate
Treatment of Cultured Glioma Cells

| CELL LINE | DURATION OF DRUG EXPOSURE | DRUG | $ED_{50}{}^a$ |
|---|---|---|---|
| 1% 9L/FPGS | 4 hrs | EDX | 605 nM |
| 10% 9L/FPGS | 4 hrs | EDX | 337 nM |
| 20% 9L/FPGS | 4 hrs | EDX | 134 nM |
| 9L/FPGS | 4 hrs | EDX | 20 nM$^f$ |

$^a ED_{50}$ = drug dose which caused 50% cell death, calculated by using Sigma Plot 3.0, which employs curve-fitting parameters based on the Marquardt-Levenberg method. Marquardt, D. W., Siam, J., J. Soc. Indust Appl Math 11:431–441 (1963).
$^b$The $ED_{50}$ values for 4 hour MTX pulse given in the table are derived from the dose-response curve in FIG. 1. This dose-response curve was generated twice, with identical results.
$^c$The $ED_{50}$ values for 4 hour EDX pulse given in the table are derived from the dose-response curve in FIG. 3a. This dose-response curve was generated one other time and produced $ED_{50}$ values of 1.2 $\mu$M (9L) and 26 nM (9L/FPGS), for a 46-fold shift.
$^d$In cocultures, the percent 9L/FPGS cells is given, the remaining cells are 9L.
$^e$The $ED_{50}$ values for MX treatment of 9L, 9L/FPGS, and a coculture are derived from the dose-response curves in FIG. 14a. Differences between the 9L and 9L/FPGS $ED_{50}$ values between FIGS. 1 and 4a can be attributed to interexperimental variation and the fact that the curve in FIG. 1 covers a wider range of concentrations, which can slightly alter curve-fitting.
$^f$The $ED_{50}$ values for EDX treatment of 9L, 9L/FPGS, and various cocultures are derived from the dose-response curves in FIG. 4b. Differences between these $ED_{50}$ values and those derived from FIG. 3a can be attributed to interexperimental variation and the fact that the curve in FIG. 3a covers a wide range of concentrations, which can slightly alter curve-fitting.

In Vivo Treatment of 9L and 9L/FPGS Tumors with MTX

To determine if there was an in viva difference in MTX responsiveness between tumors formed from 9L and 9L/FPGS cells, cells were injected into the flanks of nude mice, where they formed visible subcutaneous tumors two weeks later. Given the important role that duration of drug exposure plays in MTX toxicity, a fixed MTX dose with varying frequency of treatment was used (Chu, E. and Allegra, C, Antifolates," in *Cancer Chemotherapy and Biotherapy: Principles and Practice*, Chabner et al, eds., Lippincott-Raven, Philadelphia (1996), pp. 109–148).

Figure 2:
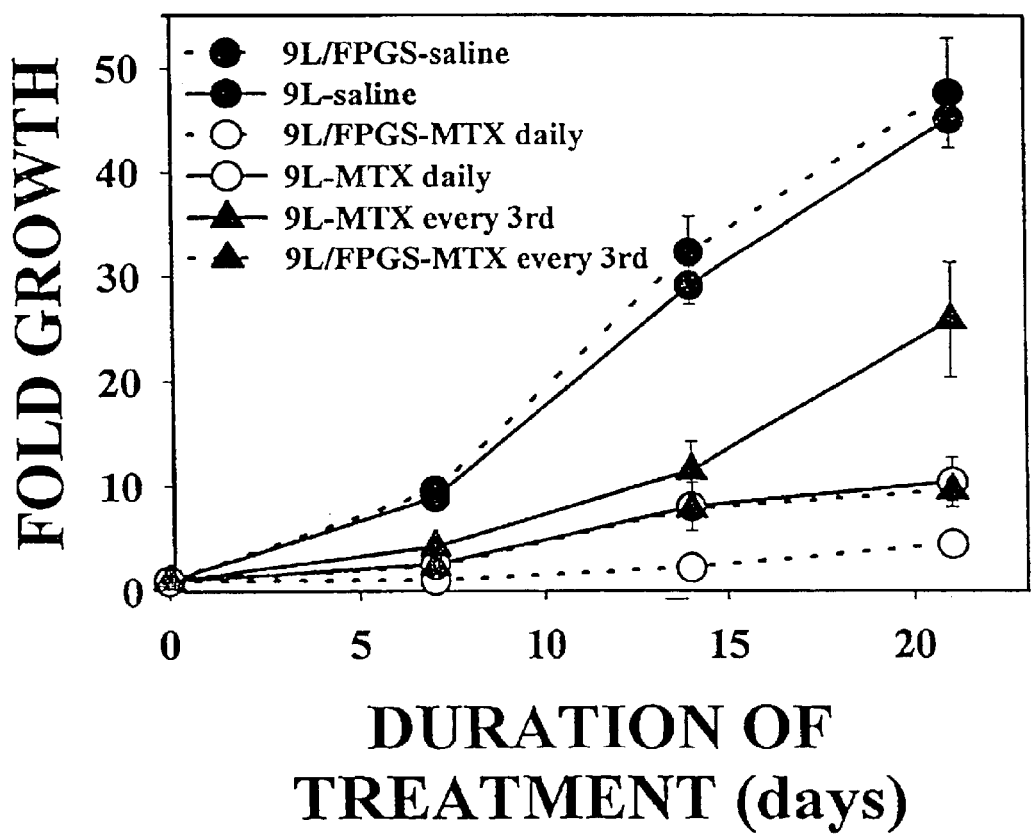
FIG. 2. Growth of subcutaneous 9L and 9L/FPGS tumors in response to different MTX regimens. Fold growth in volume from time treatment began was calculated for subcutaneous tumors formed by injecting 9L (solid lines) or 9L/FPGS (dashed lines) cells into the flanks of nude mice. Mice were treated with intraperitoneal injections of saline every day (closed circles), 9 mg MTX(kg body weight every day (open circles), or 9 mg MTX/kg body weight every third day (closed triangles). Standard errors were $\leq 5.5$-fold growth and are shown. Saline treated 9L and 9L/FPGS tumors achieved comparable fold growth (p>0.15) at each time point. MTX treatment daily for 2 weeks, daily for 3 weeks, and every third day for 3 weeks caused 9L/FPGS tumors to grow less than 9L tumors (p<0.05).

Because MTX is lethal to nude mice at lower doses than those used to treat humans, tumors implanted in nude mice are usually treated with the maximum tolerated (nonlethal) dose (MTD) of MTX. While previous studies using MTX for five consecutive days to treat nude mice tumors revealed that 15 mg/kg/day was the MTD, we found the MTD to be 9 mg/kg/day (Inaba, M., et al., *Cancer* 64:1577–1582 (1989)). Nude mice bearing 9L or 9L/FPGS tumors were therefore treated with 9 mg MTX/kg body weight daily or every third day for 21 days. Tumor volume was measured once a week, and the fold growth of each tumor relative to its volume at the time treatment commenced was measured. Then for each treatment regimen, fold growth was plotted versus time (FIG. 2). These curves reveal that 9L and 9L/FPGS tumors in saline-treated mice grew at comparable rates (p>0.15), just as the two cell lines grew at similar rates in culture. 9L/FPGS tumors responded better to both MTX treatment regimens than 9L tumors (p<0.05 for both treatment regimens after three weeks, p<0.05 for daily treatment after two weeks). After three weeks of treatment, daily MTX treatment resulted in 10-fold growth in 9L tumors and 4-fold growth in 9L/FPGS tumors; while treatment with MTX every third day led to 26-fold growth in 9L tumors and 9-fold growth in 9L/FPGS tumors. Importantly, 9L/FPGS tumors responded slightly better to MTX treatment every third day than 9L tumors did to daily MTX treatment, meaning that a reduced frequency of treatment could be achieved by tumoral expression of the FPGS cDNA, which should translate into reduced toxicity to normal cells.

Drugs Other than MTX

Antifolate drugs whose affinities for FPGS differ from MTX were tested in 4 hour pulses on 9L and 9L/FPGS cells in culture to determine if any drugs produced greater separation than MTX produced between the 9L and 9L/FPGS dose-response curves. Of the clinically useful antifolates, MTX has a relatively low affinity for FPGS, so edatrexate (EDX) and aminopterin, two drugs with slightly higher affinty for FPGS, were investigated (Chu, E. and Allegra, C, Antifolates," in *Cancer Chemotherapy and Biotherapy: Principles and Practice*, Chabner et al, eds., Lippincott-Raven, Philadelphia (1996), pp. 109–148). The affinities of these drugs for FPGS have been ranked: aminopterin>EDX>MTX—FPGS has a $K_m$ for aminopterin that is 6–7 fold lower than its $K_m$ for MTX, and its $K_m$ for EDX is 4–5 fold lower than its $K_m$ for MTX (Sirotnak, F. M., et al., *Cancer Chemotherapy and Pharmacology* 12:18–25 (1984)).

The separation between the dose-response curves for 9L and 9L/FPGS cells treated with 4 hour aminopterin pulses (data not shown) was comparable to that obtained with 4 hour MTX pulses. But when EDX was used, the dose-response curves (FIG. 3A) displayed slightly greater separation than found with the MTX dose-response curves (FIG. 1). The $ED_{50}$ of 9L cells treated with 4 hour EDX pulses was 1.2 $\mu$M, compared to 18 nM for 9L/FPGS cells (Table 3), a 67-fold difference, which is more than twice the 29-fold difference in $ED_{50}$s obtained with MTX. Pulsing with EDX concentrations between 1 nM and 10 $\mu$M generated statistically significant (p<0.025) differences in the percent survival of the two cell lines. This represents a 10,000-fold range of concentrations for which the cell lines responded differently, a much wider range than the 100-fold range of concentrations seen with MTX (FIG. 1).

In fact, the separation between the two EDX dose-response curves was large enough that there was an EDX concentration (300 nM) which was relatively nontoxic to 9L cells (greater than 90% survival) but almost completely toxic to 9L/FPGS cells (below 10% survival). In contrast, there was no MTX or aminopterin concentration that could preserve 9L cells while almost completely eliminating 9L/FPGS cells.

Figure 3B:
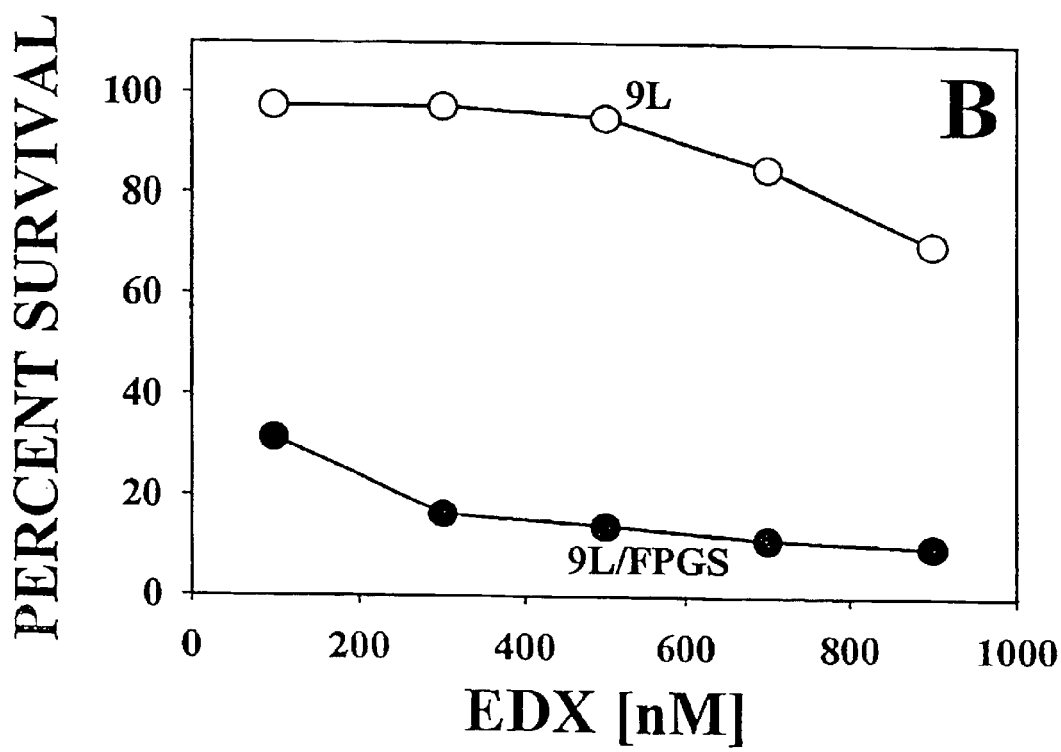

In order to demonstrate more precisely the ability of EDX to induce cytotoxicity in 9L/FPGS cells while preserving 9L cells, the data in the middle of FIG. 3A was expanded by evaluating a larger number of concentrations between 100 and 900 nM using the same 4 hour pulse protocol that had been used to generate FIG. 3A. The resulting dose-response curves (FIG. 3B) were consistently separated by differences of 60 to 80 percent survival.

Bystander Effects

The biggest limitation in cancer gene therapy is the low percentage of cells that ultimately express the transgene. The cancer gene therapy strategies that have been the most successful to date have bystander effects. The bystander effect refers to the ability of transduced tumor cells to cause cytotoxicity in neighboring nontransduced tumor cells. In drug-activating gene therapies, the bystander effect results in part from transfer of the active metabolite to nontransduced cells via facilitated diffusion, gap junctions, or apoptotic vesicles (Huber, B. E., et al., *Proceedings of the National Academy of Sciences* 91:8302–8306 (1994); Freeman, S. M., et al., *Cancer Research* 53:5274–5283 (1993)).

The simplest way to investigate the bystander effect in culture is to coculture transfected and nontransfected cells in varying ratios, treat with a drug dose that kills only transfected cells, and determine if the resulting cytotoxicity exceeds that which would be expected if only the enzyme-expressing cells had died. However, a more quantitative approach is to generate a dose-response curve for nontransfected cells, transfected cells, and a coculture and to calculate the transmission efficiency (TE) for the coculture (Friedlos, F., et al., *Journal of Medicinal Chemistry* 40:1270–1275 (1997)).

$$TE = \frac{(ED_{50}^0 - ED_{50}^N)}{(ED_{50}^0 - ED_{50}^{100})} \cdot 100$$

The superscripts 0, N, and 100 designate the $ED_{50}$ values for cultures containing 0, N, and 100% transfected cells. The transmission efficiency indicates how well the drug's effect is transmitted from transfected to nontransfected cells, i.e. a TE of 50% means the nontransfected cells in the coculture experience half the concentration of the active drug that the transfected cells experience.

9L, 9L/FPGS, and a mixture of 20% 9L/FPGS+80% 9L cells were treated with 4 hour pulses of varying EDX and MTX doses, using the same procedure used to generate FIGS. 1 and 3A, but over a slightly narrower range of concentrations. Based on the $ED_{50}$ values (Table 3) obtained by fitting this data to sigmoidal dose-response curves (FIG. 4), the TEs in cocultures containing 20% 9L/FPGS cells were 49.9% for MTX and 87.0% for EDX.

The TE value obtained with EDX was high enough to merit treating cocultures containing 10 and 1% 9L/FPGS cells with 4 hour pulses of the same EDX doses. Fitting the resulting data points to sigmoidal dose-response curves (FIG. 4B) generated $ED_{50}$ values (Table 3) which gave TE values of 63.8% for 10% 9L/FPGS cells and 33.1% for 1% 9L/FPGS cells.

The next step was to determine whether the EDX bystander effect resulted from transfer of a metabolite through the medium. Conditioned medium was harvested from 9L or 9L/FPGS cells that had been exposed to 0.3 $\mu$M EDX for 4 hours, washed extensively, and incubated for 3 days in drug-free medium. This conditioned medium was then added to 9L/BAG cells. A week later, the cells were stained for LacZ expression, which allowed colony formation to be assayed. Because multiple washes occur after EDX treatment, any EDX in the conditioned medium from treated cells at 3 days must derive from EDX that had been retained intracellularly and released after the 4 hour drug exposure. That is, even though the conditioned medium could be transferring EDX, it would have to be transferring EDX that had been released by the 9L/FPGS cells, not EDX that remained in the medium throughout the experiment.

As shown in FIG. 5, 9L/BAG cells grown with conditioned medium from 9L cells that had been pulsed with EDX formed 83% as many colonies as those grown in conditioned medium taken from non-EDX treated 9L cells. 9L/BAG cells grown with conditioned medium from 9L/FPGS cells that had been pulsed with EDX formed 47% as many colonies as 9L/BAG cells grown in conditioned medium taken from non-EDX treated 9L/FPGS cells. This suggests that part or all of the bystander effect observed during EDX treatment of cocultures results from release of a toxic metabolite from transfected cells into the medium.

Bystander Effect in Vivo

Because EDX treatment induced bystander killing of nontransfected cells in cocultures, mixtures containing 20% 9L/FPGS cells and 80% 9L cells were injected into the flanks of nude mice to establish mixed subcutaneous tumors, which were then treated with 3 mg EDX/kg/day, the dose that we observed to be the maximum nonlethal dose in nude mice.

As shown in the graphs of fold growth versus time (FIG. 6), all three tumor types displayed similar growth rates when treated with saline. Tumors formed from a mixture of 20% 9L/FPGS and 80% 9L cells displayed less growth after EDX treatment than EDX treated 9L tumors (p<0.05 after 2 and 3 weeks of daily treatment). And, while EDX treated mixed tumors displayed slightly higher fold growth than treated 9L/FPGS tumors, these differences were not significant (p>0.05 after 2 and 3 weeks of daily treatment). After two weeks of daily EDX treatment, 9L tumors had grown 8-fold, 9L/FPGS tumors had grown slightly less than 4-fold, and mixed tumors had grown slightly more than 4-fold. After three weeks of daily EDX treatment, 9L tumors had grown 10-fold; 9L/FPGS tumors experienced some growth inhibition during the third week of treatment and had only doubled in volume; and treated mixed tumors had grown 5-fold. The disparity in growth between mixed and 9L/FPGS tumors that arose between the second and third weeks of treatment was not statistically significant (p>0.05) and could have resulted from the death of 9L/FPGS cells in the mixed tumor during the first two weeks of treatment, leaving behind tumors containing a percentage of 9L cells higher than the initial 80%.

Discussion

This Example was intended to study whether FPGS gene delivery augments a tumor's antifolate susceptibility. It has been shown that downregulation of a tumor's FPGS activity via mutation leads to antifolate resistance (Pizzomo, G., et al., *Cancer Research* 48:2149(1988); Roy, K.,et al., *Journal of Biological Chemistry* 270:26918–26922 (1995); Roy, K., et al., *Journal of Biological Chemistry* 272:6903–6908 (1997); Takemura, Y., et al., *British Journal of Cancer* 75 (*suppl.* 1):31 (1997)), and that transfection of mutant CHO cells lacking FPGS activity with a plasmid bearing the FPGS cDNA enhances their susceptibility to MTX pulses (Kim, J. S., et al., *Journal of Biological Chemistry* 268:21680–21685 (1993)). It was unclear, however, whether increasing the FPGS expression of a tumor cell line already displaying intermediate FPGS enzyme activity would enhance the cell line's MTX susceptibility.

In this Example, transfection of a gliosarcoma cell line with a plasmid bearing the FPGS cDNA was shown to enhance the sensitivity of these cells to antifolate pulses in culture and to antifolate treatment in viva. Slight bystander killing of nontransfected cells upon pulse treatment of a coculture containing transfected and nontransfected cells was also demonstrated. Transfected cells displayed enhanced sensitivity in culture to 4 hour antifolate exposures, but not to 72 hour exposures. The correlation between FPGS activity and antifolate pulse susceptibility has been described and supports the applicability of FPGS gene transfer because a brief exposure better mimics clinical antifolate usage than a prolonged exposure (Kim, J. S., et al., *Journal of Biological Chemistry* 268:21680–21685 (1993)).

One criterion by which a drug-enhancing gene therapy can be evaluated is the enhancement of drug sensitivity seen in clones resulting from transfection of a tumor cell line with the cDNA for the drug-activating enzyme. The magnitude of this enhancement can be quantified by the shift in $ED_{50}$ observed between nontransfected and transected tumor cell lines. When cDNAs encoding for herpes simplex virus thymidine kinase (HSV-TK) and *E. coli* cytosine deaminase (CD) were stably transfected into 9L cells, the $ED_5$ shifts were 500-fold for ganciclovir treatment and 80-fold for 5-fluorocytosine treatment (Aghi, M., et al., *Journal of the National Cancer Institute* 90:370–380 (1998)). The 67-fold shift in $ED_{50}$ observed with EDX treatment of 9L and 9L/FPGS cells in this report is close to the shift observed for the cytosine deaminase prodrug-activating system in 9L cells. And it represents a better enhancement of sensitivity than the 8-fold decrease in $ED_{50}$ obtained when a rhabdomyosarcoma cell line was transfected with the rabbit carboxylesterase cDNA and treated with the prodrug CPT-11 (Danks, M. K., et al., *Cancer Research* 58:20–22 (1998)). Relatively large enhancement in drug sensitivity is achievable after delivery of genes like HSV-TK and CD partially because these genes are microbial, making tremendous increases in relative expression in mammalian tumors feasible. FPGS is a mammalian gene expressed to a certain extent by mammalian tumors, making relative increases in expression harder to achieve. However, two advantages of the slight FPGS expression and slight antifolate sensitivity found in tumors that would be candidates for FPGS gene transfer are: (1) tumor cells expressing foreign enzymes like HSV-TK and CD can be killed by an immune response before generating enough active drug to mediate a bystander effect, while tumor cells expressing FPGS encounter no such response; and (2) transgene expression often shuts down over time during gene therapy—loss of HSV-TK or CD expression would render ganciclovir or 5-fluorocytosine completely ineffective, while loss of expression of delivered FPGS would leave behind native FPGS activity, allowing antifolates to retain a slight anticancer effect (Roth, J. A., Cristiano, R. J., *Journal of the National Cancer Institute* 89:21–39 (1997)).

Enhanced chemosensitivity can also be appreciated by identifying drug doses which are almost completely cytotoxic to transfected cells but relatively nontoxic to nontransfected cells. In this study, such doses were not found with MTX treatment of 9L and 9L/FPGS, but 4 hours of treatment with 300 nM EDX was almost completely cytotoxic (below 10% survival) to 9L/FPGS, while preserving (above 90% survival) most 9L cells. Because antifolates can be toxic to normal tissues, having widely separated dose-response curves is important for the FPGS gene transfer approach (Chu, E. and Allegra, C, Antifolates," in *Cancer Chemotherapy and Biotherapy: Principles and Practice*, Chabner et al, eds., Lippincott-Raven, Philadelphia (1996), pp. 109–148). If most tumors are only slightly more sensitive to antifolates than normal tissues, then FPGS gene transfer may be advantageous if it can render transduced tumor cells susceptible to antifolate doses that induce minimal damage to nontransduced tumor cells—such doses that are nontoxic to tumor cells prior to gene delivery should display minimal toxicity against normal tissues.

Two factors should keep MTX toxicity directed towards tumor cells rather than normal tissues, making MTX a somewhat effective anticancer agent. First, the greater replication rate of tumor cells compared to normal cells renders them more susceptible to S-phase specific antifolates. Secondly, the somewhat greater FPGS activities of tumor cells compared to normal cells confers tumor cells with a greater capacity for drug retention and possible toxicity after drug clearance. Unfortunately, normal bone marrow and gastrointestinal epithelium replicate rapidly enough that they are somewhat MTX sensitive, and normal liver tissue possesses enough FPGS activity that it is also susceptible (Chu, E. and Allegra, C, Antifolates," in *Cancer Chemotherapy and Biotherapy: Principles and Practice*, Chabner et al, eds., Lippincott-Raven, Philadelphia (1996), pp. 109–148). Intratumoral FPGS gene transfer would enhance the disparity between tumor cells and normal cells in one of these two criteria for antifolate susceptibility and could therefore reduce the toxicity to normal tissue associated with antifolate therapy.

The anticancer effect of FPGS gene delivery could be improved by increasing the separation between the dose-response curves of transfected and nontransfected cells. One way of increasing this separation would be to generate a mutant FPGS which preferentially polyglutamylates antifolates instead of natural folates. Unfortunately, little is known about the location of the FPGS substrate binding site. Because MTX-treated tumor-bearing mice have higher levels of MTX polyglutamates in tumors than in many normal tissues and because FPGS purified from some leukemia and sarcoma cell lines has lower $K_m$ and higher $V_{max}$ values for antifolate drugs than FPGS purified from intestinal epithelium, it has been suggested that some tumors may express a tumor-specific FPGS with a unique nucleotide sequence that confers enhanced antifolate affinity (Rumberger, S. et al., *Cancer Research* 50:46394643 (1990); Kim, J. S., et al., *Journal of Biological Chemistry* 268:21680–21685 (1993); Whitehead, V. M., et al., *Cancer Research* 35:2985–2990 (1975)). If such an altered form of FPGS were cloned, it could either be used directly in FPGS gene delivery or regions where it differs from wild type FPGS could be identified and subjected to site-specific mutagenesis to further enhance its affinity for antifolates. Identification of the FPGS substrate binding site would also be easier if natural mutants with poor antifolate affinity existed. But, most antifolate resistant cell lines with altered FPGS activity display either decreased transcription or impaired translation of FPGS (Roy, K., et al., *Journal of Biological Chemistry* 270:26918–26922 (1995); Roy, K., et al., *Journal of Biological Chemistry* 272:6903–6908 (1997)). One report described an antifolate resistant cell line with impaired antifolate polyglutamylation and apparently intact folate polyglutamylation in which the last 4 exons of the 15 exon FPGS gene were deleted, but point mutations that would allow more precise characterization of the FPGS substrate binding site have not been identified (Takemura, Y., et al., *British Journal of Cancer* 75 (*suppl.* 1):31 (1997)). An alternative method of identifying the FPGS substrate binding site would be to compare the FPGS sequence to the sequence of other folate-binding enzymes. A similar approach in which the HSV-TK sequence was compared to other nucleoside kinase sequences revealed two highly conserved motifs which were subjected to random mutagenesis to create a mutant enzyme which preferentially phosphorylated the prodrug ganciclovir over the natural substrate thymidine (Whitehead, V. M., et al., *Cancer Research* 35:2985–2990 (1975); Balasubramaniam, N. K., et al., *Journal of General Virology* 71:2979–2987 (1990)).

Another way of increasing the separation between the dose-response curves of 9L and 9L/FPGS cells would be to find an antifolate that produces more widely separated dose-response curves than the drugs studied in this report. The ideal antifolate for use with FPGS gene delivery would have its inhibitory activity enhanced tremendously after polyglutamylation, and would possess intermediate affinity for FPGS, causing the drug to experience a transition from minimal to extensive polyglutamylation as FPGS activity increased by the maximum amount attainable through gene transfer. Recently, a family of antifolates which inhibit the folate-dependent enzyme thymidylate synthetase (instead of dihydrofolate reductase, which methotrexate inhibits) has been developed. These drugs are appealing for use in conjunction with FPGS gene delivery because they experience a greater enhancement in inhibitory effect after polyglutamylation than MTX (Takemura, Y., Jackman, A. L., *Anti-Cancer Drugs* 8:3–16 (1997)). Therefore, a series of experimental antifolate thymidylate synthetase inhibitors designed by collaborators are being screened on the 9L and 9L/FPGS cell lines in order to find a drug that produces wider separation of dose-response curves than that observed with MTX and EDX.

An additional important criterion for evaluating prodrug-activating gene therapies is the magnitude of the bystander effect. Because of the low transduction efficiency of most gene therapy vectors, the bystander effect is an important component of any cancer gene therapy. Although the idea of a bystander effect arising from a gene transfer strategy designed to enhance intracellular drug retention seems counterintuitive, studies of cellular MTX transport reveal that a bystander effect with FPGS gene delivery is possible. Antifolate polyglutamates fall into two categories—those that are bound to DHFR and those that are free in the cytoplasm. Polyglutamates bind DHFR very tightly—the amount of MTX-G5 bound to DHFR continues to rise 24 hours after MTX removal even though all monoglutamylated MTX detaches from DHFR 6 hours after drug removal (Jolivet, J., Chabner, B. A., *Journal of Clinical Investigation* 72:773–778 (1983)). Unlike bound polyglutamates, free polyglutamates are subject to degradation into monoglutamate by the lysosomal enzyme γ-glutamyl hydrolase. Once extracellular MA drops due to removal from medium in a pulse experiment or due to clearance in vivo, intracellular monoglutamylated MTX effluxes down its concentration gradient. The loss of intracellular monoglutamylated MTX causes lysosomal polyglutamate degradation to be favored over further MTX polyglutamylation by FPGS. It has been shown that 6 hours after removal of MTX from the medium of hepatoma cells, 43% of the total intracellular polyglutamate pool formed during MTX treatment leaves the cell as monoglutamylated MTX after intralysosomal polyglutamate cleavage (Balinska, M., et al., *Cancer Research* 41:2751–2756 (1981)). Thus, a bystander effect could arise with FPGS gene transfer through the following four step process: (1) the drug is retained intracellularly through polyglutamylation by transduced cells which survive the initial drug exposure; (2) after extracellular drug concentration drops following treatment, polyglutamates inside viable transduced cells are cleaved into the monoglutamylated form by γ-glutamyl hydrolase; (3) monoglutamylated drug effluxes down its concentration gradient out of the transduced cells; and (4) extracellular drug released from transduced cells is taken up by nontransduced cells and given a second opportunity (although at a lower concentration) to kill the nontransduced tumor cells which survived the initial drug exposure. These four steps have been studied independently using homogeneous cell lines and have been shown to occur on a time scale that is reasonable enough to support this hypothesis (Balinska, M., et al., *Cancer Research* 41:2751–2756 (1981); Kim, J. S., et al., *Journal of Biological Chemistry* 268:21680–21685 (1993)).

These studies indicate that FPGS gene delivery has a larger bystander effect in culture with EDX than MTX. While the affinities of EDX and MTX for γ-glutamyl hydrolase have not been compared, the $K_m$ of FPGS for EDX is 4–5 fold lower than for MTX; the two drugs have comparable efflux rate constants; and the influx $K_m$ of the reduced folate carrier for EDX is 4- to 14-fold lower than that for MTX (Sirotnak, F. M., et al., *Cancer Chemotherapy and Pharmacology* 12:18–25 (1984)). Thus, two of the four steps in the above hypothesis are more efficient for EDX than for MTX, which could explain why the bystander effect for EDX was stronger than that for MTX.

Even with EDX, the bystander effect of FPGS gene transfer was somewhat less substantial than that of other drug-enhancing gene therapies. Transmission efficiencies (TEs) have been used primarily to evaluate the bystander effect of the prodrug-activating enzyme nitroreductase in culture. Depending on the cell line used, the prodrug CB1954 displayed TE values between 90 and 99% for 20% cocultures (compared to 87% for EDX), above 70% for 10% cocultures (compared to 64% for EDX), and above 50% for 1% cocultures (compared to 33% for EDX). The greatest bystander effect is believed to occur with the cytosine deaminase prodrug-activating system. Although TE values have never been calculated for this system, one study describes $ED_{50}s$ that correspond to a TE value of 100% with 33% enzyme-expressing cells (Huber, B. E., et al., *Proceedings of the National Academy of Sciences* 91:8302–8306 (1994); Freeman, S. M., et al., *Cancer Research* 53: 5274–5283 (1993)). However, such a strong bystander effect can become deleterious one study of the cytosine deaminase gene therapy in an experimental brain tumor model showed therapy-related deaths due to diffluse cerebral edema resulting from extensive tumor necrosis (Dong, Y., et al., *Human Gene Therapy* 7:713–720 (1996)).

In this study, treating nude mice bearing subcutaneous tumors with the maximum tolerable antifolate dose did not eliminate tumors, but antifolate treatment in the context of FPGS gene transfer may prove more effective in humans because humans can tolerate larger antifolate doses than nude mice. While 9 mg/kg was the maximum nonlethal dose of MTX for nude mice, humans do not experience toxic side effects until 50 mg/kg—these doses correspond to peak plasma levels of 0.03 mM in a nude mouse and 0.1 mM in a human (Stoller, R. G., et al., *New England Journal of Medicine* 297:630–634 (1977)). Despite the lack of complete tumor regression, the demonstration that 9L/FPGS tumors responded slightly better to MTX treatment every third day than 9L tumors did to daily MTX treatment is important in terms of the toxicities to normal tissues caused by antifolate treatment. Increasing FPGS expression in tumor cells through gene delivery could potentially permit reductions in either MTX dose or treatment frequency. The greater toxicity of MTX polyglutamates would render transduced tumor cells more susceptible to lower MTX doses, while the greater intracellular retention of these polyglutamates would render transduced tumor cells more susceptible to lower treatment frequencies. It is believed that the duration of MTX exposure is a somewhat more important factor in its toxicity towards normal tissues than drug concentration because the S-phase specificity of MTX means that prolonged drug exposure ensures that more cells in normal tissues will be in S-phase at some point during the drug exposure (Chu, E. and Allegra, C, Antifolates," in *Cancer Chemotherapy and Biotherapy: Principles and Practice*, Chabner et al, eds., Lippincott-Raven, Philadelphia (1996), pp. 109–148). Thus, while we demonstrated that 9L/FPGS tumors responded to 3 mg/kg daily (data not shown) or 9 mg/kg every third day somewhat better than 9L cells did to 9 mg/kg daily, the ability to reduce dose frequency by a third may prove to be more important than the ability to reduce dose by a third in terms of reducing the toxicity of MTX towards normal tissues. In fact, the fact that 9L/FPGS tumors responded as well to treatment every third day as 9L tumors did to daily treatment is consistent with previous work. Studies in mice have shown that when tumors derived from cell lines with FPGS activity comparable to the 9L/FPGS cell line are treated with a single MTX injection, the tumors retain enough polyglutamates to occupy all tumor dihydrofolate reductase (DHFR) binding sites for up to 48 hours after the MTX injection (Fry, D. W., et al., Cancer Research 43:1087–1092 (1983)).

Besides lowering the duration of antifolate exposure, another way to reduce systemic MTX toxicity is to administer 5-formyltetrahydrofolate (leucovorin) after MTX therapy. Leucovorin competitively displaces MTX from DHFR. This displacement reactivates DHFR and rescues cells from MTX-induced cytotoxicity. But leucovorin rescue is less likely to occur in tumor cells because, as mentioned earlier, tumor cells have slightly greater FPGS activity than normal cells, causing them to polyglutamylate MTX to a larger extent than most normal cells. These polyglutamates have a greater affinity for DHFR than the monoglutamylated drug, and are thus harder for leucovorin to displace from the enzyme (Matherly, L. H., et al., Cancer Research 46:588 (1986)). Gene transfer of FPGS into tumor cells would enhance leucovorin's differential rescue by increasing the level of antifolate polyglutamates bound to DHFR in tumor cells.

This Example focuses on 9L, a gliosarcoma cell line that has been used extensively in experimental cancer gene therapy studies (Roth, J. A., Cristiano, R. J., Journal of the National Cancer Institute 89:21–39 (1997); Aghi, M., et al., Journal of the National Cancer Institute 90:370–380 (1998); Weizsaecker, M., et al., Journal of Neurology 224:183–192 (1981); Scharf, J. M., et al., Transgenics 1:219–224 (1994)). Because the clinical results with MTX in brain tumor therapy have been variable, MTX has not been the drug of choice for Iglioma treatment (Shapiro, W. R., Cancer Treatment Reports 61:753–756 (1977)). Despite these limitations, the 9L cell line was deemed appropriate for this preliminary investigation into FPGS gene delivery because of its repeated use in cancer gene therapy studies; because its relatively low FPGS enzymatic activity (which, according to the data in this report, may be typical of human glioma tissue) was augmentable by transfection; and because this study focused on enhancing the antifolate susceptibility of cells in culture and in vivo outside the central nervous system.

It is unclear why MTX has been unsuccessful in glioma treatment—proposed explanations include: a low replicating fraction making gliomas less responsive to S-phase specific drugs like MTX; the inability of MTX to penetrate a spheroid mass of tumor cells (the form gliomas typically assume); and altered expression of FPGS, DHFR, orotherenzymes important in MTX responsiveness. MTX's hydrophilicity does not prevent it from penetrating the blood-brain barrier, as evidenced by the fact that high dose intravenous MTX therapy usually allows for sufficient drug penetration into the CNS. For example, CNS lyinphoma is highly responsive to high dose MTX therapy (Chu, E. and Allegra, C, "Antifolates," in Cancer Chemotherapy and Biotherapy: Principles and Practice, Chabner et al, eds., Lippincott-Raven, Philadelphia (1996), pp. 109–148). In addition, CNS penetration of MTX during glioma treatment should be facilitated because the blood-brain barrier near gliomas is usually disrupted. Enhanced penetration of MTX into the CNS for glioma treatment has been achieved by combining internal carotid artery drug infusions with agents, such as mannitol, that disrupt the blood-brain barrier. In addition, human glioma cells are not intrinsically resistant to antifolates, as they are sensitive to prolonged drug exposure in culture (Terzis, A. J. A., et al., International Journal of Cancer 54:112–118 (1993)). If the low replicating fraction of gliomas contributes to the ineffectiveness of MTX in glioma treatment, then increasing the tumor's ability to polyglutamylate antifolates would increase the capacity of nonreplicating tumor cells to retain the drug until they resume replication and regain antifolate susceptibility. If low FPGS enzymatic activity, as was found in human glioblastoma and astrocytoma tissue in this Example, contributes to the ineffectiveness of MTX in glioma treatment, then FPGS gene transfer would directly address this aspect of the tumor's lack of antifolate susceptibility. And, finally, while MTX has not been used regularly to treat malignant glioma, other antifolates whose activities are also enhanced by FPGS-induced polyglutamylation are being investigated for glioma treatment. For example, EDX, the drug used in this study that produced slightly better results than MTX, is being investigated in phase II clinical trials in patients with malignant gliomas (Drinkard, L., et al., Proceedings of the American Society of Clinical Oncology 13:182 (1994)).

In addition, the approach described in this report could be applied to tumors other than gliomas. Besides gliomas, cancer gene therapy using the prodrug-activating strategy has been studied in colon carcinoma, hepatocellular carcinoma, prostate cancer, ovarian cancer, melanoma, breast cancer, lung cancer, and pancreatic cancer (Roth, J. A., Cristiano, R. J., Journal of the National Cancer Institute 89:21–39 (1997)). Some of these tumors, such as breast and colon cancers, are often treated with MTX and FPGS gene delivery could be evaluated as a means of enhancing the drug's efficacy; the other tumors are like gliomas in that MTX is not the drug of choice but could become a viable therapeutic if FPGS gene delivery substantially enhanced the drug's anticancer effect.

FPGS activity is just one variable contributing to antifolate susceptibility. Even when comparing different brain tumor cell lines, the correlation between FPGS activity and MTX susceptibility did not always hold. The $ED_{50}$ for U87 cells treated with a 4 hour MTX pulse was 30 $\mu$M (Table 3), over 10-fold higher than that of 9L. The greater sensitivity of 9L to MTX pulses was inconsistent with U87's slightly greater FPGS activity (Table 1), reflecting the fact that FPGS activity is probably not the only parameter affecting MTX sensitivity that may differ between these two cell lines—other differences could be levels of reduced folate carrier, replication rates, DHFR expression, or γ-glutamyl hydrolase levels. Therefore, FPGS activity only correlates definitively with MTX pulse sensitivity in cell lines which express varying levels of FPGS activity but derive from the same parental cell line, such as 9L and 9L/FPGS (Rumberger, S. et al., Cancer Research 50:4639–4643 (1990)).

There has been some discussion about whether or not the enhancement in therapeutic efficacy caused by MTX polyglutamylation makes MTX a prodrug (Chabner, B. A., Journal of Clinical Investigation 76:907–912(1985)). A prodrug is a chemical that is inert at all doses but can be converted into a highly toxic chemical by a specific prodrug-activating enzyme (Connors, T. A., Gene Therapy 2:702–709 (1995)). In reality, all prodrugs become toxic at high enough doses, even in the absence of prodrug-activating enzyme, because cells have alternative enzymes which activate the prodrug to some extent at high enough doses. Therefore, all prodrug-activating gene therapies are in reality drug-enhancement systems. MTX's chemotherapeutic activity makes it distinct from chemicals such as 5-fluorocytosine and ganciclovir which can only affect non-transduced tumors at doses that substantially exceed their maximum tolerable doses. However, while these prodrugs require gene delivery in order to become active at reasonable doses, gene delivery could enhance a tumor's existing antifolate sensitivity. This enhancement would increase the likelihood of a successful outcome with high dose antifolate therapy or, in patients experiencing antifolate toxicity, would permit reductions in dose or dose frequency without compromising therapeutic efficacy (Chu, E. and Allegra, C, Antifolates," in *Cancer Chemotherapy and Biotherapy: Principles and Practice*, Chabner et al, eds., Lippincott-Raven, Philadelphia (1996), pp. 109–148). Because the enhancement in chemosensitivity observed after FPGS gene transfer is comparable to that observed with some other prodrug-activating gene therapies and because of the presence of a slight bystander effect in culture and in vivo, the FPGS gene transfer strategy merits further investigation, regardless of whether the antifolate drugs used are to be considered prodrugs or drugs.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A method of enhancing the cytotoxic sensitivity of neoplastic cells to an antifolate drug, said neoplastic cells expressing an endogenous level of folypolyglutamyl synthetase (FPGS), said method comprising:
    (a) delivering directly to said neoplastic cells a vector, said vector comprising a DNA sequence encoding, operably linked to a promoter, wherein said FPGS is expressed in said neoplastic cells at a level higher than the endogenous FPGS level of said neoplastic cells;
    (b) treating the neoplastic cells in step (a) with an antifolate drug that is polyglumated by FPGS; and
    (c) enhancing the cytotoxic sensitivity of said neoplastic cells to said antifolate drug.

2. The method of claim 1, wherein said FPGS is a mammalian FPGS.

3. The method of claim 2, wherein said mammalian FPGS is a human FPGS.

4. The method of claim 2, wherein said antifolate drug is methotrexate, edatrexate, aminopterin, or a thymidylate synthetase inhibitor.

5. The method of claim 4, wherein said antifolate drug is methotrexate or edatrexate.

6. The method of claim 5, wherein said antifolate drug is edatrexate.

7. The method of claim 3, wherein said antifolate drug is methotrexate.

8. The method of claim 3, wherein said antifolate drug is edatrexate.

9. The method of claim 1, wherein said vector is a viral vector.

10. The method of claim 7, wherein said vector is a viral vector.

11. The method of claim 8, wherein said vector is a viral vector.

12. The method of claim 9, wherein said viral vector is a retrovirus, adenovirus, adeno-associated virus, herpes virus, poliovirus, papillomavirus, or lentivirus.

13. The method of claim 12, wherein said viral vector is a retrovirus, adenovirus, or herpes virus.

14. The method of claim 1, wherein said vector is non-viral.

15. The method of claim 1, wherein said vector is a an attenuated bacterial vector, a cationic liposome, a fusogenic liposome, a DNA-adenovirus conjugate, a DNA-protein complex, a non-viral T7 autogene vector, a starburst polyamidoamine dendrimer, or a cationic peptide.

16. The method of claim 14, wherein said vector is a an attenuated bacterial vector.

17. The method of claim 1, wherein said vector is delivered directly to said neoplastic cells by direct injection of nucleic acid, particle-mediated gene transfer, or receptor-mediated gene transfer.

18. The method of claim 1, wherein said neoplastic cells are breast cancer or colon cancer cells.

19. The method of claim 1, wherein said vector is delivered directly to said neoplastic cells by inoculation.

20. A method of enhancing the cytotoxic sensitivity of neoplastic cells to methotrexate or edatrexate, said neoplastic cells expressing an endogenous level of folypolyglutamyl synthetase (FPGS), said method comprising:
    (a) delivering directly to said neoplastic cells a vector, said vector comprising a DNA sequence encoding, operably linked to a promoter, wherein said FPGS is expressed in said neoplastic cells at a level higher than the endogenous FPGS level of said neoplastic cells;
    (b) treating the neoplastic cells in step (a) with methotrexate or edatrexate; and
    (c) enhancing the cytotoxic sensitivity of said neoplastic cells to said methotrexate or edatrexate.

21. The method of claim 20, wherein said vector is delivered directly to said neoplastic cells by inoculatin.

* * * * *

UNITED STATES PATENT AND TRADEMARK OFFICE
CERTIFICATE OF CORRECTION

PATENT NO. : 6,770,632 B1
DATED : August 3, 2004
INVENTOR(S) : Aghi et al.

It is certified that error appears in the above-identified patent and that said Letters Patent is hereby corrected as shown below:

<u>Title page,</u>
Item [54], Title, please delete the following: "FOLYPOLYGLUTAMYL SYNTHETASE GENE TRANSFER TO ENHANCE ANTIFOLATE" and insert therein -- FOLYPOLYGLUTAMYL SYNTHETASE GENE TRANSFER TO ENHANCE ANTIFOLATE DRUG SENSITIVITY --.
Item [56], References Cited, OTHER PUBLICATIONS,
"Garrow, T.A. et al.," references, please delete "folylpoly (λ-glutamate)" and insert therein -- folylpoly (γ-glutamate) --.
"Taylor, S.M. et al.," references, please delete "Folylpoly-$\mu$-glutamate" and insert therein -- Folylpoly-γ-glutamate --.

<u>Column 29,</u>
Line 38, please delete "folypolyglutamyl" and insert therein -- folylpolyglutamyl --.
Line 41, please delete "encoding, operably" and insert therein -- encoding FPGS, operably --.
Line 47, please delete "polyglumated" and insert therein -- polyglutamated --.

<u>Column 30,</u>
Lines 24 and 29, please delete "bacteral" and insert therein -- bacterial --.
Line 28, please delete "a".
Line 41, please delete "folypolyglutamyl" and insert therein -- folylpolyglutamyl --.
Lines 44-45, please delete "encoding,operably" and insert therein -- encoding FPGS, operably --.
Line 54, please delete "inoculatin" and insert -- inoculation --.

Signed and Sealed this

Twenty-third Day of November, 2004

JON W. DUDAS
*Director of the United States Patent and Trademark Office*